US012584910B2

(12) United States Patent
Berney et al.

(10) Patent No.: US 12,584,910 B2
(45) Date of Patent: Mar. 24, 2026

(54) SENSING ASSEMBLY

(71) Applicant: Analog Devices International Unlimited Company, Limerick (IE)

(72) Inventors: Helen Berney, Limerick (IE); Youri Victorvitch Ponomarev, Eindhoven (NL); Joyce Wu, Boston, MA (US); Christophe Antoine, Limerick (IE)

(73) Assignee: Analog Devices International Unlimited Company, Limerick (IE)

( * ) Notice: Subject to any disclaimer, the term of this patent is extended or adjusted under 35 U.S.C. 154(b) by 174 days.

(21) Appl. No.: 18/273,632

(22) PCT Filed: Jan. 21, 2022

(86) PCT No.: PCT/EP2022/051379
§ 371 (c)(1),
(2) Date: Jul. 21, 2023

(87) PCT Pub. No.: WO2022/157328
PCT Pub. Date: Jul. 28, 2022

(65) Prior Publication Data
US 2024/0125779 A1     Apr. 18, 2024

Related U.S. Application Data

(60) Provisional application No. 63/140,726, filed on Jan. 22, 2021.

(51) Int. Cl.
*G01N 33/543* (2006.01)
(52) U.S. Cl.
CPC ................................ *G01N 33/5438* (2013.01)

(58) Field of Classification Search
CPC ....................... G01N 33/5438; G01N 33/4836
See application file for complete search history.

(56) References Cited

U.S. PATENT DOCUMENTS

| | | | |
|---|---|---|---|
| 5,508,171 | A | 4/1996 | Walling et al. |
| 7,867,369 | B2 | 1/2011 | Bhullar et al. |
| 8,999,724 | B2 | 4/2015 | Holt et al. |
| 9,164,054 | B2 | 10/2015 | Iyengar et al. |
| 9,215,995 | B2 | 12/2015 | Gottlieb et al. |

(Continued)

FOREIGN PATENT DOCUMENTS

| | | |
|---|---|---|
| CN | 111316072 A | 6/2020 |
| EP | 0950895 A2 | 10/1999 |

(Continued)

OTHER PUBLICATIONS

International Search Report and Written Opinion issued in International Patent Application No. PCT/EP2022/051379 on May 6, 2022.

(Continued)

*Primary Examiner* — C. Sun
(74) *Attorney, Agent, or Firm* — ArentFox Schiff LLP

(57) ABSTRACT

The present disclosure provides a sensing assembly for sensing an analyte. The sensing assembly comprises multiple test electrodes configured to provide signals from multiple independent measurements in response to the analyte. Alternatively or additionally, the multiple test electrodes are configured to produce different transient responses in response to a given concentration of the analyte.

19 Claims, 16 Drawing Sheets

(56)                    References Cited

U.S. PATENT DOCUMENTS

| | | | |
|---|---|---|---|
| 9,810,656 | B2 | 11/2017 | Davis et al. |
| 9,874,538 | B2 | 1/2018 | Johnson et al. |
| 10,448,872 | B2 | 10/2019 | Wolfe et al. |
| 10,520,501 | B2 | 12/2019 | Johnson et al. |
| 10,548,530 | B2 | 2/2020 | Kinser |
| 10,598,625 | B2 | 3/2020 | Crooks et al. |
| 2004/0219523 | A1 | 11/2004 | Stanton et al. |
| 2005/0023137 | A1 | 2/2005 | Bhullar et al. |
| 2006/0134713 | A1 | 6/2006 | Rylatt et al. |
| 2006/0272958 | A1 | 12/2006 | Lee |
| 2009/0020502 | A1 | 1/2009 | Bhullar et al. |
| 2013/0098777 | A1* | 4/2013 | Gaustad ................. C12Q 1/005 |
| | | | 205/780.5 |
| 2013/0231542 | A1 | 9/2013 | Simpson et al. |
| 2018/0275088 | A1 | 9/2018 | Huff et al. |
| 2018/0299399 | A1 | 10/2018 | Keshavjee et al. |
| 2018/0317833 | A1* | 11/2018 | Heikenfeld ........ G01N 33/5438 |
| 2019/0232282 | A1 | 8/2019 | Pierson et al. |
| 2020/0237276 | A1 | 7/2020 | Oja et al. |

FOREIGN PATENT DOCUMENTS

| | | | |
|---|---|---|---|
| EP | 1530043 | A1 | 5/2005 |
| JP | 08-285814 | A | 11/1996 |
| JP | 2004-309462 | A | 11/2004 |
| JP | 2020-509373 | A | 3/2020 |
| WO | 2010050898 | A1 | 5/2010 |
| WO | 2015007369 | A1 | 1/2015 |

OTHER PUBLICATIONS

Gaser N. Abderlasoul et al., "DNA aptamer-based non-faradaic impedance biosensor for detecting *E. coli*", Analytica Chimica Acta, Vo. 1107, Apr. 22, 2020, pp. 135-144.

Yeon Seok Kim et al., "Specific detection of oxytetracycline using DNA aptamer-immobilized interdigitated array electrode chip", Analytica Chimica Acta, Feb. 23, 2009; 634(2):250-4. doi: 10.1016/j.aca.2008.12.025. Epub Dec. 25, 2008. PMID: 19185128.

Jun Yan et al., "Immobilizing Enzymes onto Electrode Arrays by Hydrogel Photolithography to Fabricate Multi-Analyte Electro-chemical Biosensors", ACS Applied Materials & Interfaces, Feb. 16, 2010, 2 (3), 748-755.

Yuting Zhang et al., "Electrochemical dual-aptamer biosensor based on nanostructured multielectrode arrays for the detection of neuronal biomarkers" Royal Society of Chemisty, Nanoscale, Jul. 11, 2020, 12, pp. 16501-16513.

* cited by examiner

SENSING ASSEMBLY

CROSS-REFERENCE TO RELATED APPLICATIONS

This application is a 35 U.S.C. § 371 National Stage Application of International Patent Application No. PCT/EP2022/051379, filed Jan. 21, 2022, which application claims the benefit of and priority to U.S. Provisional Patent Application No. 63/140,726, filed Jan. 22, 2021, the contents of each of which applications are hereby incorporated by reference herein in their entireties.

FIELD OF THE DISCLOSURE

This disclosure relates to a sensing assembly, for example a biosensor or chemical assay, for sensing an analyte, a sensing assembly for sensing a plurality of analytes which are different from each other, and a system and method for determining a concentration of an analyte in a sample matrix.

BACKGROUND

Various biosensor and chemical assay designs are known for sensing analytes. Analytes may, for example, include biomarkers, such as hormones, established to assist in patient monitoring and/or diagnosis.

In, for instance, standard enzyme-linked immunosorbent assays (ELISA), employed for quantifying analytes such as peptides, proteins, antibodies, and hormones, a recognition element for selectively interacting with, for example binding, the analyte of interest is immobilized on a suitable support. For example, an antigen is immobilized on the support and then complexed with an antibody that is linked to an enzyme.

In biosensors and assays, such as ELISA, it has been found to be challenging to make quantitative measurements of analytes over a wide range of concentrations. Typically there is a trade off between sensitivity and the range of concentrations that can be detected.

SUMMARY OF THE DISCLOSURE

The present disclosure provides a sensing assembly for sensing an analyte. The sensing assembly comprises multiple test electrodes configured to provide signals from multiple independent measurements in response to the analyte. Alternatively or additionally, the multiple test electrodes are configured to produce different transient responses in response to a given concentration of the analyte.

In certain embodiments a sensing assembly is provided that comprises a test electrode arrangement. The test electrode arrangement comprises a plurality of test electrodes. Each of the test electrodes has an analyte interaction portion configured to selectively interact with the analyte. A saturation limit at which the analyte interaction portion is saturated with the analyte is defined for each of the test electrodes. The respective saturation limits vary between the test electrodes. The sensing assembly further comprises a set of control electrodes providing a set of control electrode areas, with each control electrode area being configured for providing a control measurement which is independent of the analyte. Each control electrode area is provided for one of the test electrodes.

In certain embodiments a sensing assembly is provided for sensing a plurality of analytes which are different from each other. The sensing assembly comprises a first test electrode arrangement. The first test electrode arrangement comprises a plurality of first test electrodes. Each of the first test electrodes comprises a first analyte interaction portion configured to selectively interact with a first analyte. A first saturation limit at which the first analyte interaction portion is saturated with the first analyte is defined for each of the first test electrodes. The respective first saturation limits vary between the first test electrodes. The sensing assembly further comprises a second test electrode arrangement and a second set of control electrodes. The second test electrode arrangement comprises a plurality of second test electrodes. Each of the second test electrodes comprises a second analyte interaction portion configured to selectively interact with a second analyte which is different from the first analyte. A second saturation limit at which the second analyte interaction portion is saturated with the second analyte is defined for each of the second test electrodes. The respective second saturation limits vary between the second test electrodes. The sensing assembly further comprises at least one set of control electrodes providing a set of control electrode areas, with each control electrode area being configured for providing a control measurement which is independent of the analytes. Each control electrode is provided for one of the first test electrodes and/or one of the second test electrodes.

In certain embodiments, a system is provided for determining a concentration of an analyte in a sample matrix. The system comprises a sensing assembly for sensing the analyte. The sensing assembly comprises a test electrode arrangement. The test electrode arrangement comprises a plurality of test electrodes. Each of the test electrodes has an analyte interaction portion configured to selectively interact with the analyte. A saturation limit at which the analyte interaction portion is saturated with the analyte is defined for each of the test electrodes. The respective saturation limits vary between the test electrodes. The sensing assembly further comprises a set of control electrodes providing a set of control electrode areas, with each control electrode area being configured for providing a control measurement which is independent of the analyte. Each control electrode area is provided for one of the test electrodes. The system comprises a signal processing unit and a concentration determination unit. The signal processing unit is configured to process signals received from the plurality of test electrodes, and process signals received from the set of control electrode areas. The concentration determination unit is configured to, based on the signals processed from the plurality of test electrodes and on the signals processed from the set of control electrode areas, determine the concentration of the analyte in the sample matrix.

In certain embodiments, a method is provided for determining a concentration of an analyte in a sample matrix. The method comprises processing signals received from a plurality of test electrodes. Each of the test electrodes comprises an analyte interaction portion configured to selectively interact with the analyte. A saturation limit at which the analyte interaction portion is saturated with the analyte is defined for each of the test electrodes; the respective saturation limits varying between the test electrodes. The method comprises processing signals received from a set of control electrodes. The set of control electrodes provide a set of control electrode areas, with each control electrode area being configured for providing a control measurement which is independent of the analyte. Each control electrode area is provided for one of the test electrodes. The method further comprises determining the concentration of the analyte in the sample matrix based on the signals processed from the plurality of test electrodes and on the signals processed from the set of control electrode areas.

BRIEF DESCRIPTION OF THE DRAWINGS

The present invention will now be described in more detail with reference to the accompanying drawings, which are not intended to be limiting.

DETAILED DESCRIPTION

Figure 1:
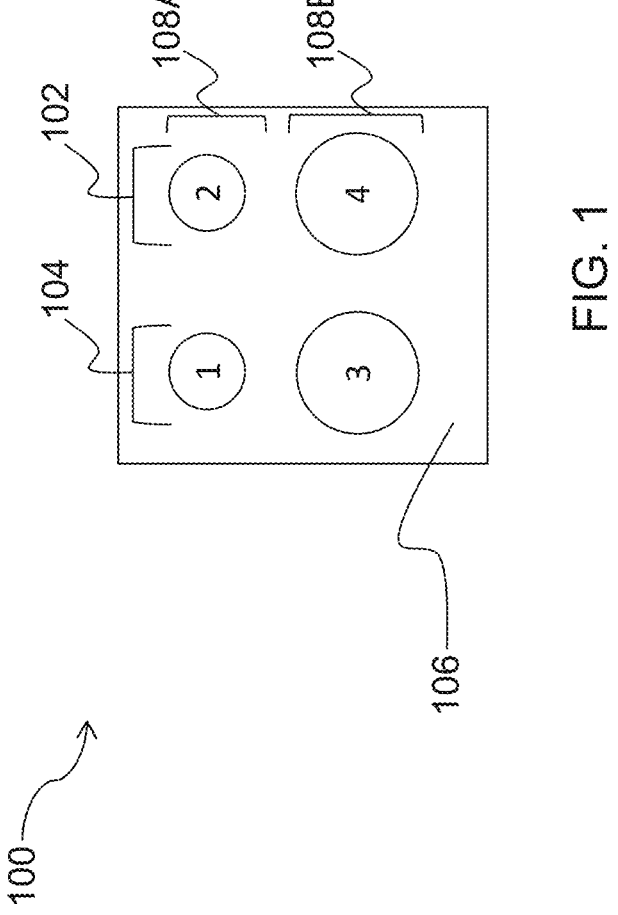
FIG. 1 provides a schematic plan view of a sensing assembly according to an example.

Various analyte sensing techniques are known which utilise analyte binding technology. A capture species with specificity for the particular analyte, in other words ligand, can be used to bind the analyte. Such binding can be detected in various ways, such as colorimetrically, via fluorescence, or electrochemically.

Quantitative measurement of analytes over a wide range of concentrations is a challenge. Typically there is a trade off between sensitivity and the range of concentrations that can be detected.

Certain embodiments of the present disclosure provide a sensing assembly for sensing an analyte. Such a sensing assembly may comprise a test electrode arrangement having a plurality of test electrodes, with each of the test electrodes having an analyte interaction portion configured to selectively interact with the analyte.

Multiple test electrodes may be configured to provide signals from multiple independent measurements in response to the analyte. Alternatively or additionally, the multiple test electrodes may be configured to produce different transient responses in response to a given concentration of the analyte.

Multiple signal inputs may be used to determine analyte concentration, rather than, for example, solely relying on equilibrium or endpoint data.

Without wishing to be bound by any particular theory, such multiple test electrodes may assist, in at least some embodiments, to provide the sensing assembly with a broader dynamic range, in other words a broader range from the lowest to the highest concentration of the analyte that can be reliably sensed by the sensing assembly. Alternatively or additionally, in some embodiments the multiple test electrodes can assist to provide greater accuracy in determining the analyte concentration, owing to the provision of several measurement signals, for example several independent measurement signals.

In certain embodiments of the present disclosure the respective saturation limits vary between the test electrodes. The saturation limit is defined by the analyte concentration in the sample matrix at which the analyte interaction portion of the respective test electrode is saturated with the analyte. This may be indicated by no further change to the respective test electrode signal resulting from contact with analyte concentrations higher than the analyte concentration defining the saturation limit, under otherwise the same conditions.

In some embodiments, the saturation limit may be regarded as an analyte binding capacity of the respective test electrode. The saturation limit may be reached, in other words, when all available sites of the analyte interaction portion are interacting with, e.g. binding, the analyte.

The terms "analyte concentration" or "concentration of the analyte" as used herein may, in certain embodiments, refer to the activity of the analyte. The activity of the analyte may provide a measure of the effective concentration of the analyte in a sample matrix. The activity may assist to account, for instance, for analyte-analyte interactions in the sample matrix, which may become more relevant at higher analyte concentrations. The above-identified "concentration" terms are nonetheless used herein for convenience.

The upper concentration limit of the sensing assembly may be extended by the test electrode arrangement including test electrodes having higher saturation limits. Moreover, the rate of change of the signal may also be dependent on the analyte concentration. Different transient responses to a given analyte concentration may be observed from the lower saturation limit test electrodes relative to the higher saturation limit test electrodes.

It is noted that in at least some biosensor/assay configurations, a so-called "hook effect" is observed at analyte concentrations beyond the saturation limit. The measured or observed concentration may actually begin to decrease in such a high analyte concentration regime.

In some embodiments, including test electrodes having higher saturation limits in the sensing assembly may assist to displace the high analyte concentration regime at which such a hook effect is observed to higher analyte concentrations.

The analyte may, for example, be selected from a molecular species, a metal ion, a virus, and a microorganism. Particular mention is made of biomarkers, such as a cytokine or a hormone, since these have relevance in the context of patient monitoring, and diagnostic testing. The analyte may, for instance, be a hormone selected from an eicosanoid, a steroid, an amino acid, amine, peptide or protein.

In a non-limiting example, the analyte interaction portion is defined by capture species provided adjacent a surface of the respective test electrode. In such an example, the capture species are configured to selectively interact with the analyte.

Any suitable capture species can be selected for this purpose, according to the analyte which is intended to be sensed by the sensing assembly. For example, the capture species may comprise an antibody with specificity for a particular antigen. In such an example, the analyte may take the form of the antigen.

More generally, the capture species may, in some embodiments, comprise at least one selected from a protein, a peptide, a carbohydrate, and a nucleic acid.

The protein may, for example, be an enzyme, such as an enzyme having specificity for the analyte. In other non-limiting examples, the protein is an antibody. In the latter case, the analyte may be an antigen which is selectively bound by the antibody.

The capture species may, for instance, comprise or be defined by an antigen. In this case, the analyte may be a species, such as an antibody, which is selectively bound by the antigenic capture species. The antigen may be or comprise, for example, a protein, a peptide, a carbohydrate, such as a polysaccharide or glycan.

In an embodiment, the capture species comprises an aptamer. An aptamer may be defined as an oligonucleotide or peptide configured to bind the analyte. Such an aptamer may, for example, be configured to interact with, for example bind, various analyte types, such as small molecules, for example amino acids or amines, proteins, metal ions, and microorganisms.

In some non-limiting examples, the aptamer is functionalized with an electro-active moiety, for example a redox-active moiety, and is configured such that a conformational change of the aptamer upon selectively interacting with, for example binding, the analyte causes a change in the proximity of the electro-active moiety with respect to the surface of the respective test electrode.

Particularly in examples in which the test electrodes are configured for determining a change in current associated with the selective interaction with the analyte, such a change in proximity of the electro-active moiety with respect to the surface of the respective test electrode can cause, or at least contribute to, the determined current change. Thus, the aptamer being functionalized with such an electro-active moiety can assist with amperometric sensing of the analyze.

The proximity change resulting from the aptamer interacting with, for example binding, the analyte could, for instance, result in the electro-active moiety moving closer to the surface of the respective test electrode than when the aptamer is not interacting with the analyte. In such examples, electron transfer between the electro-active moiety and the respective test electrode may become faster, such as to contribute to an increase in current in the respective test electrode upon interaction between the analyte and the aptamer.

In alternative non-limiting examples, the proximity change resulting from the aptamer interacting with, for example binding, the analyte could result in the electro-active moiety moving further from the surface of the respective test electrode than when the aptamer is not interacting with the analyte.

In such examples, the aptamer may be regarded as being conformationally configured in the absence of the analyte such that the electro-active moiety, for example redox-active moiety, is proximal to, or even in contact with, the test electrode surface, thereby providing a baseline signal.

In such cases, a decrease in current in the respective test electrode upon interaction between the analyte and the aptamer may be observed. Thus, the greater the concentration of analyte, the greater the decrease in the current. Specific non-limiting examples of this will be described herein below with reference to FIGS. 4 to 8.

Any suitable electro-active moiety may be included in the aptamer for this purpose, such as methylene blue.

In some embodiments, each test electrode surface is functionalized with the capture species. Such functionalization can be achieved in any suitable manner, such as by covalently or non-covalently immobilizing the capture species to the surface.

For example, thiol-terminated capture species, such as a thiol-terminated aptamer, can be immobilized, for example grafted, onto the surface of a noble metal, for example gold, electrode.

In certain embodiments, a parameter relating to an amount of the capture species for each of the test electrodes determines the saturation limit of the respective test electrode. Thus, different amounts of capture species are provided for, for example immobilized on, each test electrode.

When, for example, the test electrode surface is functionalized with the capture species, the parameter may comprise an area of the surface functionalized with the capture species.

Such varying of the area of the surface functionalized with the capture species may be achieved in any suitable manner. In a non-limiting example, the conductive areas of the test electrodes vary in the test electrode arrangement. In this way, the saturation limits of the test electrodes vary due to (at least) the variation of the conductive areas functionalized with the capture species.

In such an example, the area of the surface functionalized with the capture species may correspond to the conductive area of the respective test electrode.

The test electrodes with different areas may, for instance, be arranged in an array, for example with the test electrodes being arranged in the array in order of increasing area. Such an array may be regarded, for example, as an analyte titration platform.

Any suitable variation of the saturation limits of the test electrodes can be considered, for example according to the desired dynamic range of the sensing assembly. For example, the test electrodes may be configured, for example sized, to enable analyte concentration sensing across a logarithmically scaled range of concentrations.

In a non-limiting example, the functionalization of each the conductive areas with the capture species may be uniform for each of the test electrodes. This may permit the same protocol for functionalizing the test electrode, for example using the same reagent drop size, reagents, washes, etc., to be used for each of the test electrodes in the test electrode arrangement. It may thus be the differently sized conductive areas which determine the varying saturation limits of the test electrodes.

A relatively high analyte concentration may saturate the smaller area test electrodes, but not the larger area test electrodes. The rate of change of the signal may also be dependent on the concentration, as previously described. Thus, the data generated, for example the signal changes from the smaller area to larger area electrodes and the rate of change of the signal(s), can be used to quantify the analyte.

In examples in which the capture species comprises an aptamer, and the proximity change resulting from the aptamer interacting with, for example binding, the analyte results in the electro-active moiety of the aptamer moving away from the surface of the respective test electrode, a current may be generated in the test electrodes when no analyte is interacting with the aptamer.

The larger the area of the test electrode the more capture molecules may be immobilized on its surface, and the larger the starting current in the virgin state test electrode in which no analyte is interacting with the aptamer.

In other non-limiting examples, the area of the surface functionalized with the capture species may be within, and thus not correspond to, the conductive area of the respective test electrode. In such examples, the analyte interaction portion may terminate at a boundary, which boundary can be identified using a suitable technique, for example atomic force microscopy. The area of the analyte interaction portion delimited by the thus identified boundary can then be determined.

Alternatively or additionally to the parameter comprising the area of the surface functionalized with the capture species, the parameter may comprise a density of the capture species on the test electrode surface. A greater density of the capture species on the surface may assist to provide a larger saturation limit of the respective test electrode.

Varying the density of the capture species on the test electrode surfaces may be implemented in any suitable manner, such as by varying the concentration of the capture species, for example aptamer, solution used for functionalizing the surfaces. A more concentrated solution may provide a higher density, for example packing density, of the capture species on the surface of the respective test electrode.

In some embodiments, the capture species may be held adjacent the surface by a membrane. The membrane may permit the analyte to pass therethrough, and thereby be captured by the capture species disposed between the test electrode surface and the membrane. A non-limiting example of this will be described herein below with reference to FIG. 10.

In such non-limiting examples in which the capture species is disposed between the respective test electrode surface and such a membrane, the parameter may comprise a concentration of the capture species in a solution provided between the membrane and the surface. Thus, by varying the concentration of the capture species for each of the test electrodes, the saturation limits of the test electrodes can be varied.

In some embodiments, the test electrode arrangement comprises a plurality of units, with each unit defining one of the test electrodes and comprising a number of test electrode sub-units. In such embodiments, the number of test electrode sub-units in each unit at least partly determines the saturation limit of the respective test electrode.

It is noted that a test electrode sub-unit parameter relating to an amount of the capture species for each of the test electrode sub-units may further contribute to determining the saturation limit of the respective test electrode. Thus, the more general description provided above in relation to the parameter relating to the amount of capture species for each of the test electrodes is applicable to the test electrode sub-units. The test electrode sub-unit parameter may, for example, comprise at least one of an area of the surface of the respective test electrode sub-unit functionalized with the capture species and a density of the capture species on the surface of the respective test electrode sub-unit.

At least some, and in some examples each, of the test electrode sub-units may have the same area as each other. This may, for instance, enable the same reagent drop size, reagents, washes, etc., to be used for each of these test electrode sub-units. The saturation limit may nonetheless vary between the units (at least) because of the different numbers of test electrode sub-units included in each of the units. A non-limiting example of such a test electrode arrangement will be described herein below with reference to FIGS. 14 and 15.

In some non-limiting examples, each unit, and in some cases one or more test electrode sub-units within a unit, may be individually addressable. This may assist to enhance the configurability to the test electrode arrangement.

More generally, the test electrodes may comprise, or be formed of, any conductive material suitable for use in the sensing assembly, such as a noble metal, for example gold or platinum, or titanium nitride.

More generally, the key to at least some of the embodiments of the present disclosure is that a multiplicity of sites having different saturation limits, for example by having different areas functionalized with the capture species, may allow a wider range of concentrations to be determined.

In at least some embodiments of the present disclosure, the sensing assembly further comprises a set of control electrodes providing a set of control electrode areas, with each control electrode area being configured for providing a control measurement which is independent of the analyte. In such embodiments, each control electrode area is provided for one of the test electrodes.

For example, none of the control electrode areas may include an analyte interaction portion configured to selectively interact with the analyte. In this manner, each of the control electrode areas may permit a control measurement to be taken which is independent of analyte, and in particular independent of the concentration of the analyte.

The set of control electrodes may be arranged in any suitable manner, such as in the form of an array. In examples in which the test electrodes are also arranged in an array, the test electrodes array and the control electrodes array may, for instance, extend parallel with each other.

In certain embodiments, the control electrode areas vary relative to each other. Such variation of the control electrode areas may assist the set of control electrodes to provide a control arrangement for each of the test electrodes.

More generally, the test electrode arrangement and the set of control electrodes are arranged to receive a sample matrix. The sample matrix, for example blood, urine, sweat, tears, etc., may (potentially) contain the analyte.

In some non-limiting examples, the test electrode arrangement and the set of control electrodes are mounted on a common substrate, for example a common semiconductor substrate, such as a silicon wafer. An example of this will be explained below with reference to FIG. 1.

In alternative examples, the test electrode arrangement is mounted on a first substrate, for example a first semiconductor substrate, and the set of control electrodes is mounted on a second substrate, for example a second semiconductor substrate, such as a (second) silicon wafer.

The test electrode arrangement and the set of control electrodes may, for instance, be arranged in a suitable vessel or fluidics system, for example a microfluidics system. The sample matrix may be received in the vessel or fluidics system, and thus the sample matrix may be brought into contact with the test electrode arrangement and the set of control electrodes.

In some embodiments, the control electrode areas are configured for non-selective interaction with the sample matrix. The set of control electrodes may be regarded in such embodiments as providing a negative control measurement. Such a negative control measurement may, for example, determine a signal or signals associated with non-selective interaction, for example non-specific binding, of the sample matrix with the control electrode areas.

In a non-limiting example, the control electrode areas are functionalized with a control aptamer configured to not interact with the analyte. Such a control aptamer may, for instance, comprise an electro-active moiety, for example a redox-active moiety.

For example, the electro-active moiety of the control aptamer may be proximal the surface of the respective control electrode area, and since the control aptamer does not interact with the analyte the signal, for example current signal, associated with the control electrode area may remain constant, or at least substantially constant, in the presence of the analyte. Thus, each control electrode area in this non-limiting example may be configured for providing a control measurement which is independent of the analyte. The term "substantially constant" in this context is to account for the relatively small signal changes resulting from the sample matrix contacting the control electrode area.

This behavior, for example amperometric behavior, of such a control aptamer-functionalized control electrode area contrasts with that of, for instance, the aptamer-functionalized test electrodes described above. In examples in which the electro-active moiety is caused to move towards the surface of respective test electrode by the interaction of the analyte with the aptamer, the current may increase in the presence of the analyte. In alternative examples in which the electro-active moiety is caused to move away from the surface of the respective test electrode by the interaction of the analyte with the aptamer, the current may decrease in the presence of the analyte. The differing amperometric behaviors of the test electrodes and control electrode areas will be illustratively described in more detail herein below with reference to FIGS. 4 to 8.

It is noted that any suitable electro-active moiety may be included in the control aptamer, such as methylene blue.

In certain embodiments, the control electrode areas are configured to selectively interact with a non-analyte species included in the sample matrix. The set of control electrodes may be regarded in such embodiments as providing a positive control measurement. Such a positive control measurement may be based, for instance, on interaction with a common/ubiquitous species, for example molecule, in the sample matrix, such as hemoglobin when the sample matrix comprises or is blood, or urea when the sample matrix comprises or is urine.

More generally, varying of the control electrode areas may permit an ordering of the control electrode areas by increasing size, and the varying of the saturation limits permits a further ordering of the test electrodes by increasing saturation limit.

Thus, a series of test electrode-control electrode area pairs may be defined according to the ordering and the further ordering such that the smallest control electrode area is paired with the test electrode having the smallest saturation limit to the largest control electrode area being paired with the test electrode having the largest saturation limit.

Such a series of test electrode-control electrode area pairs can be arranged in any suitable manner. For example, the series may extend linearly, for example on the surface of a common substrate, such as a common semiconductor substrate.

In an embodiment, for consecutive test electrode-control electrode area pairs of the series, an incremental change in the control electrode areas corresponds to a further incremental change in the saturation limits of the test electrodes. The variation of the control electrode areas corresponding to, for example being the same as or proportional to, the variation in saturation limits of the test electrodes may assist meaningful comparison to be made between the test electrode signal and the control electrode signal of each test electrode-control electrode pair.

In this way, contribution to signals arising from selective interaction of the analyte interaction portion of the test electrodes with the analyte can be properly distinguished from contribution to such signals which may merely be associated with the sample matrix.

In an embodiment, each control electrode area corresponds to the area of the surface of one of the test electrodes functionalized with the capture species.

In non-limiting examples in which the area of the test electrodes functionalized with the capture species varies, the control electrode area may, for instance, be the same as the area functionalized with capture species of one of the test electrodes.

In a particular non-limiting example, the sensing assembly comprises a series, for example sets, of test electrode-control electrode area pairs, and the test electrodes have varying areas functionalized with capture species, for example an aptamer. For each pair, the control electrode area may correspond to, for example be the same as, the area functionalized with capture species of the test electrode.

This area may, for example, have a diameter spanning the range of 1 μm to 500 μm, such as 10 μm to 100 μm.

The area may determine the absolute signal generated. This may mean that a single analyte concentration in the sample matrix can generate multiple signal inputs, for example absolute change in signals from smaller to larger area test electrode-control electrode area pairs, and the rate of change of the signal(s), that can be deconvoluted to give a specific concentration of analyte.

More generally, the set of control electrodes may comprise, or be formed of, any suitable conductive material, such as a noble metal, for example gold or platinum, or titanium nitride.

In some embodiments, the set of control electrodes comprises a plurality of portions, for example conductive portions, which are each individually addressable. In such embodiments, the set of control electrode areas may each be defined by addressing one or more of the plurality of portions.

Addressing/activating one, or certain combinations, of the portions, for example via a suitable switch arrangement, may thus permit selection of each control electrode area. The control electrode area may be selected according to the saturation limit of one of the test electrodes, as previously described.

Figure 9:
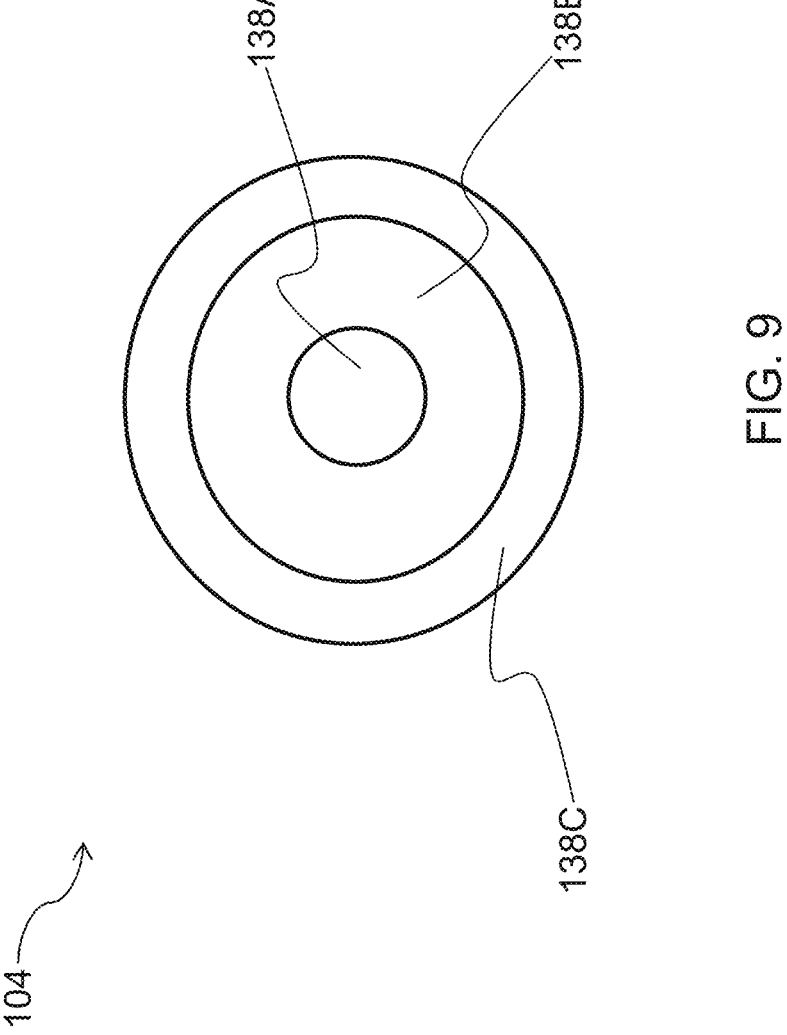
FIG. 9 provides a schematic plan view of a set of control electrodes according to an example.

The plurality of portions may be arranged in any suitable manner, such as in the form of concentric circular, elliptical or arcuate portions, as in the non-limiting example depicted in FIG. 9, and/or as a plurality of interdigitated portions. Such arrangements may assist, for example, to save space on the substrate on which the set of control electrodes is arranged.

The analyte sensing assembly may be compatible with any suitable sensing, for example electrochemical sensing, principle. In some embodiments, the analyte sensing assembly comprises an electrochemical cell including a working electrode assembly and a counterelectrode. In such embodiments, the working electrode assembly may comprise the test electrode arrangement.

The test electrode arrangement may thus be configured for determining a change in current associated with said selective interaction with the analyte. Such amperometric analyte sensing has been mentioned in the context of some of the non-limiting examples described above.

The working electrode assembly may also comprise the set of control electrodes. Thus, the set of control electrodes may also be configured for determining a change in current associated with the sample matrix contacting the control electrode areas.

The counter electrode may act as a cathode or anode to the working electrode assembly, for example the test electrode arrangement and the set of control electrodes.

In some embodiments, the electrochemical cell further comprises a reference electrode. The reference electrode may constitute a site of a known chemical reaction having a known redox potential. Any suitable reference electrode may be employed, such as a saturated calomel, silver/silver chloride, or a copper/copper sulfate reference electrode.

The fixed redox potential of the reference electrode may provide a reference point for the redox potential of the working electrode assembly. The potential generated within the electrochemical cell may derive from the working electrode assembly, and current may be measured via the potential of the working electrode assembly set against the fixed potential of the reference electrode. The signal/signal change resulting from, for example, interaction of the analyte with the analyte interaction portion(s) of the test electrode(s) and/or interaction of the sample matrix with the control electrode area(s), may be produced in the external circuit of the electrochemical cell from this difference in potential.

In some embodiments, the sensing electrode assembly may comprise, for example as an alternative or in addition to the above-described electrochemical cell, a capacitance and/or impedance determination assembly. Thus, the principles of the present disclosure can, for example, be implemented in the form of a capacitive and/or impedimetric sensing array.

Such a capacitance and/or impedance determination assembly may comprise a further electrode arrangement, with at least some of the test electrodes of the test electrode arrangement being spaced apart from the further electrode arrangement such as to enable determination of capacitance and/or impedance between said at least some of the test electrodes and the further electrode arrangement.

The further electrode arrangement can take any suitable form. In some non-limiting examples, the further electrode arrangement itself comprises one or more of the test electrodes, such that each of the spatially separated "plates" of the capacitance and/or impedance determination assembly comprises an analyte interaction portion. Examples of this will be described herein below with reference to FIGS. 16 to 18. In other non-limiting examples, the further electrode arrangement does not include such an analyte interaction portion, and may, for example, be defined by an unfunctionalized electrode.

The capacitance and/or impedance determination assembly may further comprise the set of control electrodes, with the set of control electrodes being spaced apart from the further electrode arrangement such as to enable determination of capacitance and/or impedance between the set of control electrodes and the further electrode arrangement.

In certain embodiments, a system for determining a concentration of an analyte in a sample matrix comprises the sensing assembly according to any of the embodiments and examples described herein, and a signal processing unit configured to process signals received from the plurality of test electrodes and process signals received from the set of control electrode areas. The system further includes a concentration determination unit configured to, based on the signals processed from the plurality of test electrodes and on the signals processed from the set of control electrode areas, determine the concentration of the analyte in the sample matrix.

In at least some embodiments, the concentration determination unit of the system is configured to determine the concentration of the analyte based on one or more differential signals between the signals processed from the plurality of test electrodes and the signals processed from the set of control electrode areas.

The concentration determination unit may, in certain embodiments, be configured to determine the concentration based on (at least) the absolute change in signals in the test electrode-control electrode pairs, and the rate of change of the signals.

The signal processing unit and the concentration determination unit may be implemented in any suitable manner, with software and/or hardware, to perform the various functions required. One or both of the units may, for example, employ one or more microprocessors programmed using software (for example, microcode) to perform the required functions. Examples of processor components that may be employed in various embodiments of the present disclosure include, but are not limited to, conventional microprocessors, application specific integrated circuits (ASICs), and field-programmable gate arrays (FPGAs).

In various implementations, one or both of the signal processing unit and the concentration determination unit may be associated with one or more non-transitory storage media such as volatile and non-volatile computer memory such as RAM, PROM, EPROM, and EEPROM. The non-transitory storage media may be encoded with one or more programs that, when executed on one or more processors and/or controllers, perform the required functions. Various storage media may be fixed within a processor or controller or may be transportable, such that the one or more programs stored thereon can be loaded into the signal processing unit and/or the concentration determination unit.

In some non-limiting examples, the system includes a user interface, such as a display, for communicating the analyte concentration determined by the concentration determination unit.

Alternatively or additionally, the system may include a communications interface device, such as a wireless transmitter, configured to transmit the analyte concentration determined by the concentration determination unit to an external device, such as a personal computer, tablet, smartphone, remote server, etc.

In certain embodiments, the sensing assembly is configured for sensing a plurality of analytes which are different from each other. In such embodiments, the sensing assembly comprises a first test electrode arrangement. The first test electrode arrangement comprises a plurality of first test electrodes. Each of the first test electrodes comprises a first analyte interaction portion configured to selectively interact with a first analyte. A first saturation limit at which the first analyte interaction portion is saturated with the first analyte is defined for each of the first test electrodes. The respective first saturation limits vary between the first test electrodes.

In such embodiments, the sensing assembly further comprises a second test electrode arrangement. The second test electrode arrangement comprises a plurality of second test electrodes. Each of the second test electrodes comprises a second analyte interaction portion configured to selectively interact with a second analyte which is different from the first analyte. A second saturation limit at which the second analyte interaction portion is saturated with the second analyte is defined for each of the second test electrodes. The respective second saturation limits vary between the second test electrodes.

The sensing assembly further comprises at least one set of control electrodes providing a set of control electrode areas, with each control electrode area being configured for providing a control measurement which is independent of the analytes. Each control electrode area is provided for one of the first test electrodes and/or one of the second test electrodes.

In a non-limiting example, the at least one set of control electrodes comprises a first set of control electrodes and a second set of control electrodes. In such an example, the first set of control electrodes provides a set of first control electrode areas, with each first control electrode area being provided for one of the first test electrodes, and the second set of control electrodes provides a set of second control electrode areas, with each second control electrode area being provided for one of the second test electrodes.

The sensing assembly may be configured to sense a plurality, such as two, three, four, five, six, or more analytes which are different from each other. To this end the sensing assembly may comprise second, third, fourth, fifth, sixth, or nth test electrode arrangements, and second, third, fourth, fifth, sixth, or nth sets of control electrodes.

In a non-limiting example, the first, second, etc. test electrodes and the first, second, etc. sets of control electrodes may, for instance, be provided on a single substrate, such as on a single semiconductor substrate. For example, the first, second, etc. test electrodes and the first, second, etc. sets of control electrodes may be provided on a common slide, chip or strip. An example of this will be described herein below with reference to FIG. 11.

In an embodiment, each of the plurality of analytes is independently selected from a molecular species, a metal ion, a virus, and a microorganism.

In a non-limiting example, one or more of the plurality of analytes is or are a biomarker, such as a cytokine or a hormone, since these have relevance in the context of patient monitoring, and diagnostic testing.

One or more, for example each, of the plurality of analytes may, for instance, be a hormone selected from an eicosanoid, a steroid, an amino acid, amine, peptide or protein.

In a non-limiting example, the first, second, etc. analytes may be hormones, such as two or more of estradiol (E-2), luteinising hormone (LH), progesterone, and follicle-stimulating hormone (FSH).

Other than being configured to sense different analytes, the first test electrode arrangement and the second test electrode may be as described above in relation to the test electrode arrangement. Similarly, the first and second sets of control electrodes may be as described above in respect of the set of control electrodes.

FIG. 1 provides a schematic plan view of a sensing assembly 100 according to an example. The sensing assembly 100 comprises multiple, in this case two, test electrodes 102, and a corresponding number of, in this case two, control electrode areas 104.

In the non-limiting example depicted in FIG. 1, the test electrodes 102 and the control electrode areas 104 are provided, for example formed using semiconductor lithographic techniques, on a common substrate 106, for example a silicon substrate 106.

The sensing assembly 100 shown in FIG. 1 comprises a series, for example sets, of test electrode-control electrode area pairs 108A, 108B, and the test electrodes 102 have varying areas functionalized with capture species configured to interact with, for example bind, the analyte. In this case, the capture species comprises an aptamer. For each pair 108A, 108B in this non-limiting example, the control electrode area is the same as the area functionalized with capture species of the test electrode 102.

Figure 2:
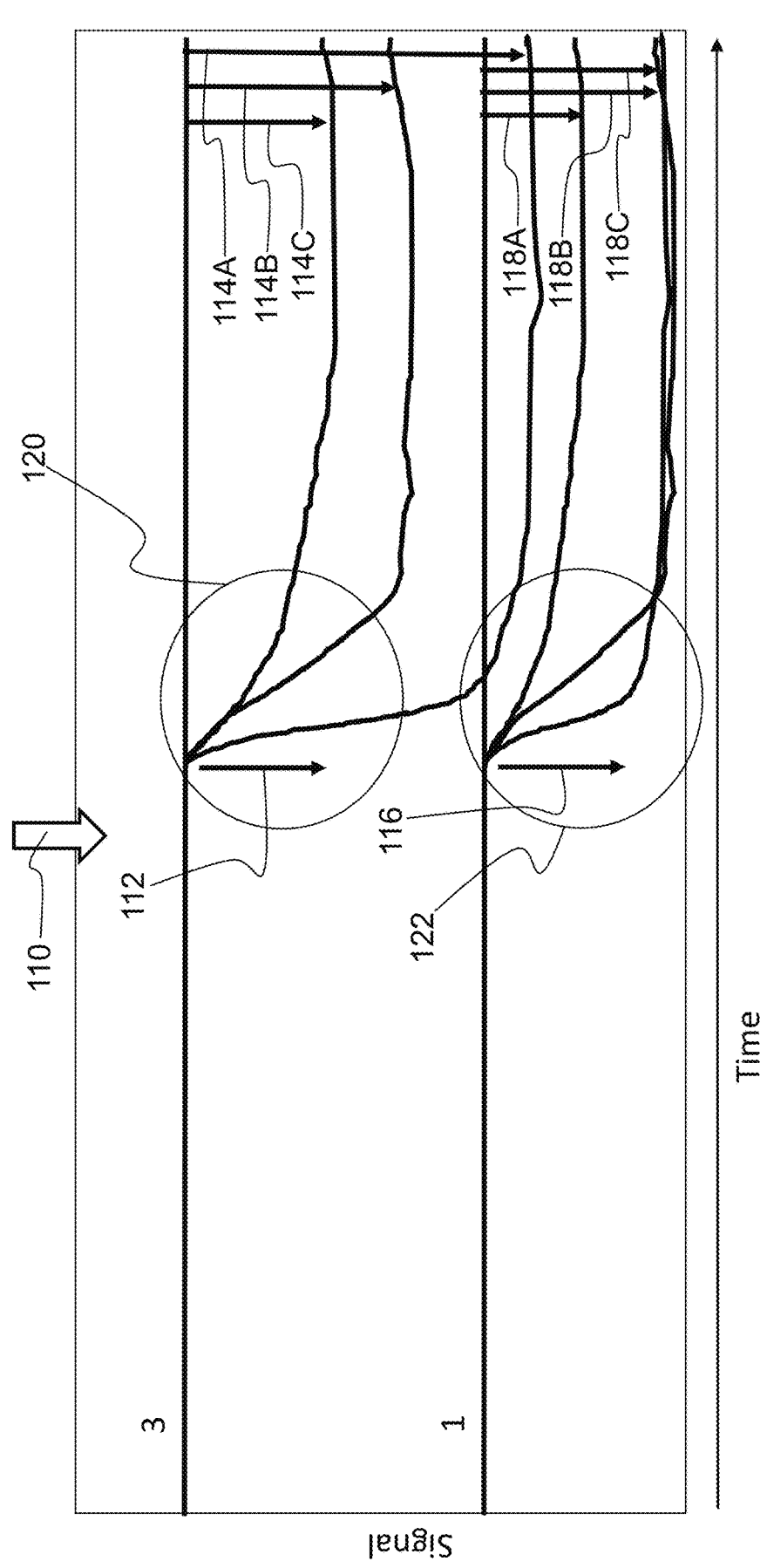
FIG. 2 provides graphs of sensor signal versus time for the sensing assembly shown in FIG. 1.

As shown in FIG. 1, the control electrode areas 104 are numbered 1 and 3, and the test electrodes 102 are numbered 2 and 4. FIG. 2 provides graphs of sensor signal versus time for the sensing assembly 100 shown in FIG. 1 when sensing sample matrices having various analyte concentrations.

In this non-limiting example, an electro-active moiety is included in a control aptamer (not visible in FIG. 1) which functionalizes a surface of each control electrode area 104. The electro-active moiety, for example methylene blue, is disposed proximal the surface of the respective control electrode area.

A sample matrix containing analyte is introduced at point 110 in FIG. 2. Since the analyte does not interact with, for example bind, to either of the control electrode areas 104, the signals for the control electrode areas numbered 1 and 3 are substantially unchanged upon addition of the analyte, as shown. The absolute signal is nonetheless larger for the control electrode area numbered 3 than for the control electrode area numbered 1 because the former has a larger area functionalized with the control aptamer.

FIG. 2 provides plots for three sample matrices, each having a different analyte concentration from the others. The signal for the test electrode numbered 4 decreases as the concentration of the analyte in the respective sample matrix increases, as denoted by the arrow 112. The is because the aptamer comprises an electro-active moiety which is caused to move away from the surface of the respective test electrode by the interaction of the analyte with the aptamer, as previously described. The signal changes with increasing analyte concentration in the sample matrix, as shown in plots 114A, 114B, and 114C, with more of the surface aptamers binding the analyte.

The signal for the test electrode numbered 2 also decreases as the concentration of the analyte in the respective sample matrix increases, as denoted by the arrow 116. The sample matrix for plot 118A is the same as for plot 114A. Similarly, the sample matrices for plots 118B and 118C are the same as those for plots 114B and 114C respectively.

The plot 118A points to the analyte concentration being such that only some of the available aptamer binds the analyte. Plots 118B and 118C point to the test electrode numbered 2 being saturated with analyte because the overall signal change is the same in spite of the sample matrix for plot 118C having a higher analyte concentration.

It is evident from the circled regions 120 and 122 in FIG. 2 that different transient responses to a given analyte concentration may be observed from the lower saturation limit test electrode numbered 2 relative to the higher saturation limit test electrode numbered 4. Referring, in particular, to the circled region 122, it is evident that whilst the overall signal change is the same for plots 1188 and 118C, the rate of change of signal in plot 118B appears discernably different from that in plot 118C. The rate of change is significantly faster in plot 118C, in which the concentration of analyte is higher.

Thus, a single analyte concentration in the sample matrix can generate multiple signal inputs: absolute change in current from smaller to larger area test electrode-control electrode area pairs 108A, 108B, and different rates of change of the current. Such multiple signal inputs may be deconvoluted to give a specific concentration of the analyte. This approach may offer enhanced accuracy of concentration-determination, compared with a concentration derived from a single signal input.

More generally, the electrical, for example, current signal(s) may be monitored in the time domain in order to enable the rate of signal change to be determined.

The rate of signal change, and the absolute value of the signal(s), and in some examples further signal inputs, may be used to determine the analyte concentration.

Figure 3:
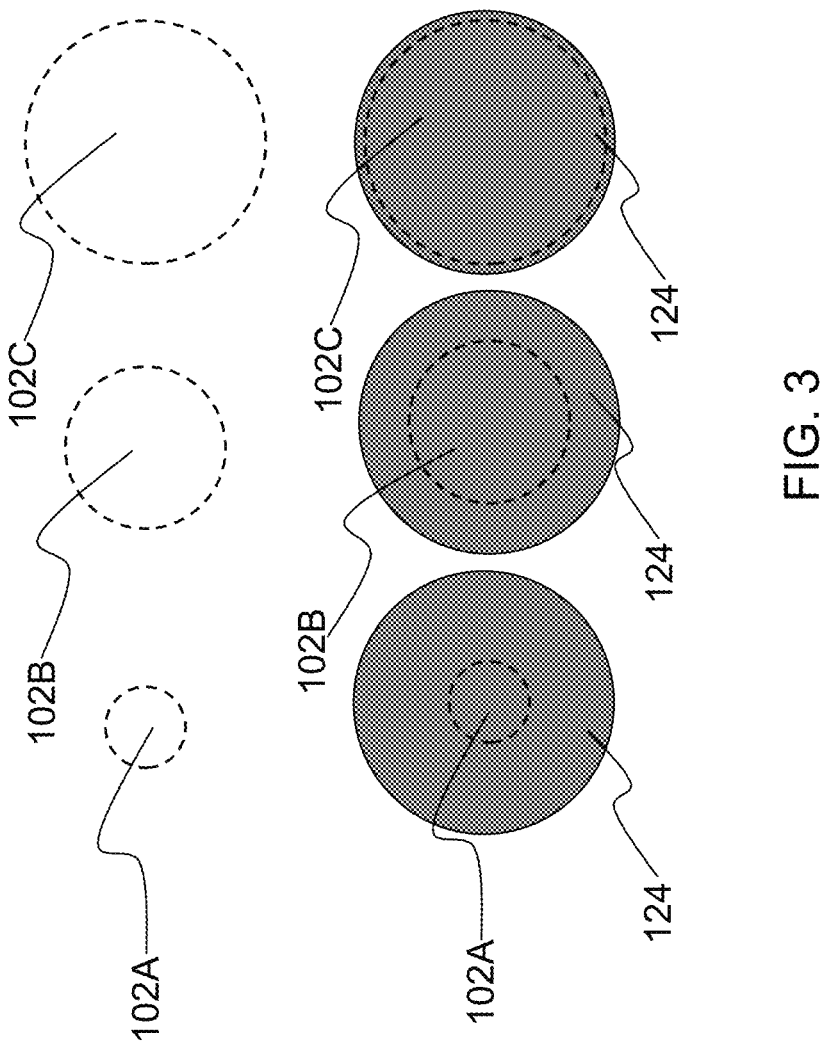
FIG. 3 provides a schematic plan view of electrodes of varying area, and a schematic depiction of immobilization of a capture species on the electrodes.

FIG. 3 provides, in the upper pane, a schematic plan view of an array test electrodes 102A, 102B, 102C. The conductive area of each test electrode 102A, 102B, 102C is different from the others, as shown. This may permit the same protocol to be used for functionalizing each test electrode. In this respect, the lower pane of FIG. 3 shows the same reagent drop size 124 being used for each of the test electrodes 102A, 102B, 102C in the test electrode arrangement. Similarly, the same reagents, washes, etc., may be used for each of the test electrodes 102A, 102B, 102C. This may provide a convenient way of realizing test electrodes 102A, 102B, 102C with varying saturation limits.

The drop size 124, for example corresponding to the largest diameter of each drop in a plane parallel with the surface of the substrate on which the electrode areas are provided, may be, for example, 10 μm to 150 μm, such as 50 μm to 150 μm, such as 100 μm. The electrode areas may, for instance, have a diameter ranging from 1 μm to 100 μm, such as 10 μm to 100 μm.

Immobilisation of the capture species may utilize that same size drop, for example 100 μm, but the pick up/functionalization area is based in this example on the conductive area of the electrode.

It is noted that in examples in which the control electrode areas 104 are surface functionalized, for example with a control aptamer, differently sized control electrode areas 104 may be realized in a similar manner using the same reagent drop size, reagents, washes, etc.

Figure 4:
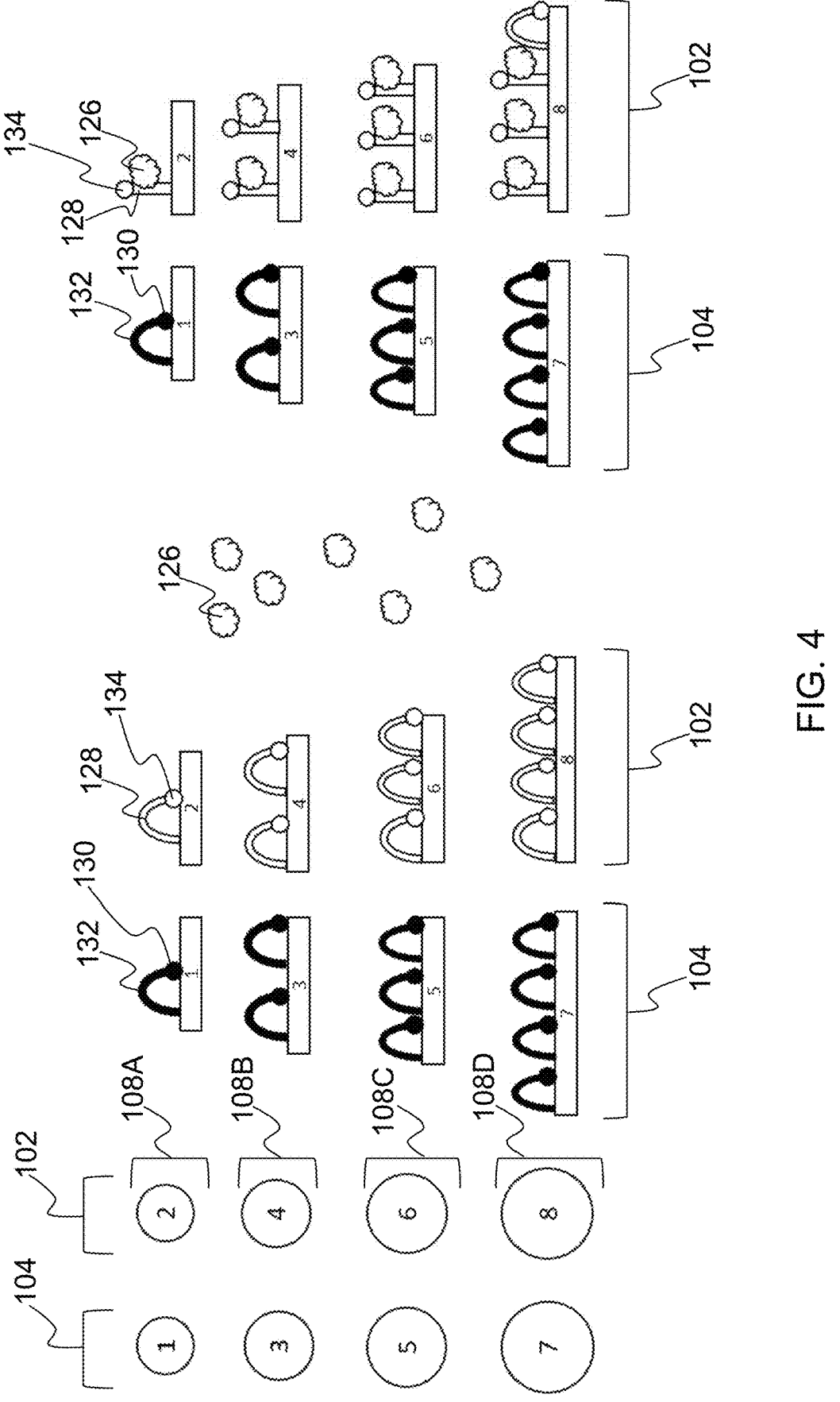
FIG. 4 schematically depicts analyte sensing using a sensing assembly according to another example, when the analyte concentration in a sample matrix is relatively high.

FIG. 4 schematically depicts analyte sensing using a sensing assembly 100 according to another example. The sensing assembly 100 comprises multiple, in this case four, test electrodes 102, and a corresponding number of, in this case four, control electrode areas 104.

It is noted, more generally, that any number of test electrodes 102 (and control electrode areas 104) can be contemplated, such as two, three, four, five, six, seven, eight, nine, ten, or more, for example according to the desired dynamic range for the sensing assembly 100.

The sensing assembly 100 shown in FIG. 4 comprises a series, for example sets, of test electrode-control electrode area pairs 108A, 108B, 108C, 108D, and the test electrodes 102 have varying areas functionalized with capture species configured to interact with, for example bind, the analyte 126. In this case, the capture species comprises an aptamer 128. For each pair 108A, 108B, 108C, 108D in this non-limiting example, the control electrode area 104 is the same as the area functionalized with capture species of the test electrode 102.

In this non-limiting example, an electro-active moiety 130 is included in a control aptamer 132 which functionalizes a surface of each control electrode area 104. The electro-active moiety 130, for example methylene blue, is disposed proximal the surface of the respective control electrode area 104.

Figure 5:
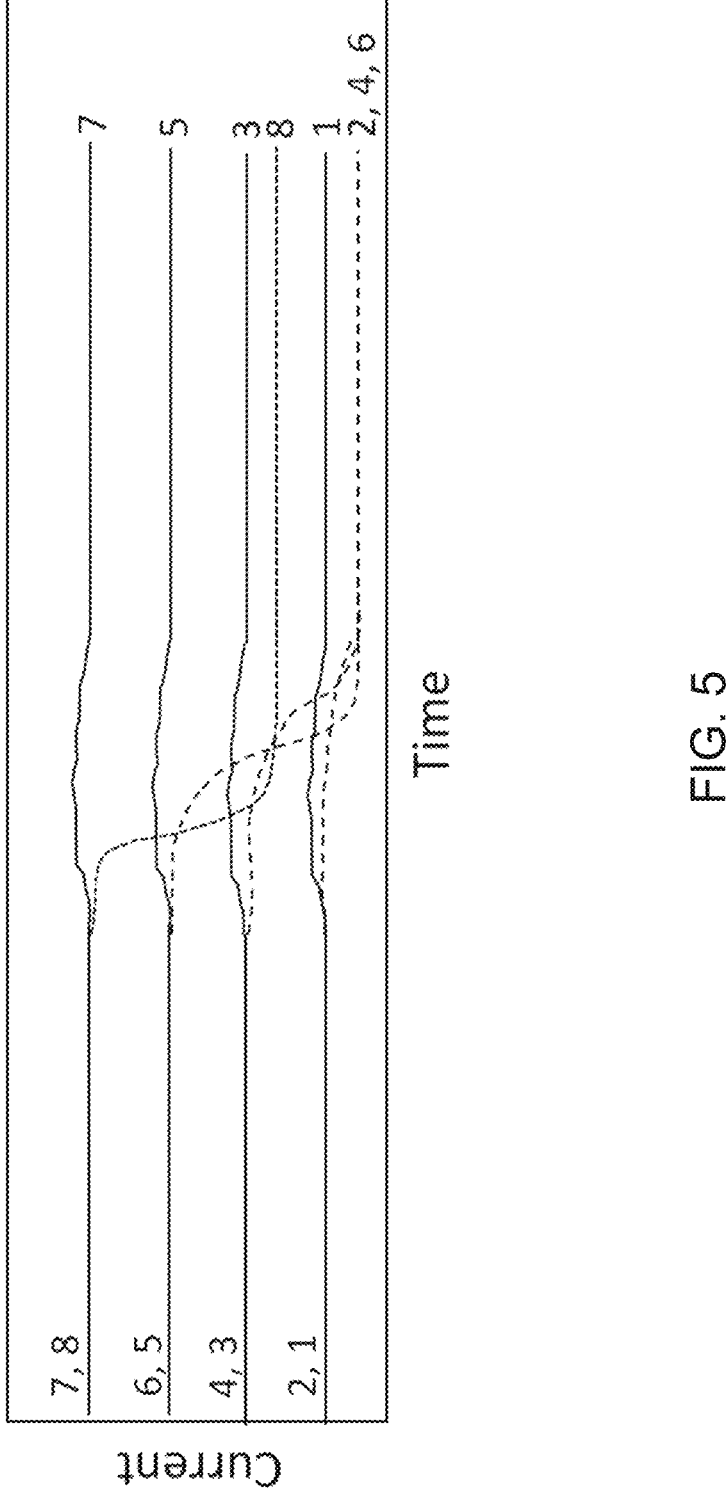
FIG. 5 provides graphs of sensor signal versus time for the sensing assembly and sample matrix shown in FIG. 4.

As schematically depicted in FIG. 4, the conformational change caused by the aptamer 128 interacting with, for example binding, the analyte 126 results in the electro-active moiety 134, for example methylene blue, included in the aptamer 128 moving further from the surface of the respective test electrode 102 than when the aptamer 128 is not interacting with the analyte 126. As shown in FIG. 5, a decrease in current in the respective test electrode 102 upon interaction between the analyte 126 and the aptamer 128 is correspondingly observed.

As shown in FIG. 4, the control electrode areas 104 are numbered 1, 3, 5 and 7, and the test electrodes are numbered 2, 4, 6 and 8. FIG. 5 provides graphs of sensor signal versus time for the sensing assembly and sample matrix shown in FIG. 4, in which the concentration of the analyte 126 in the sample matrix is relatively high.

This relatively high analyte 126 concentration results in saturation of the test electrodes numbered 2, 4 and in FIG. 4. As shown in FIG. 5, the current in each the test electrodes numbered 2, 4 and 6 decreases, and approaches about zero current in this particular example. The test electrode numbered 8 is not saturated, since not all the aptamer 128 on the surface of this test electrode is interacting with the analyte 126. Thus, the current in the test electrode numbered 8 does not fall to about zero current in this case.

Whilst there is substantially no change in the current in the control electrode areas 104 because the control aptamer 132 does not bind the analyte 126, a relatively small signal is nonetheless observed for each of the control electrode areas 104 which is associated with interaction with the sample matrix. As shown in FIG. 5, the absolute signal increases with increasing control electrode area, as previously described in respect of FIGS. 1 and 2, such that the largest absolute signal is observed with the control electrode area numbered 7.

Figure 6:
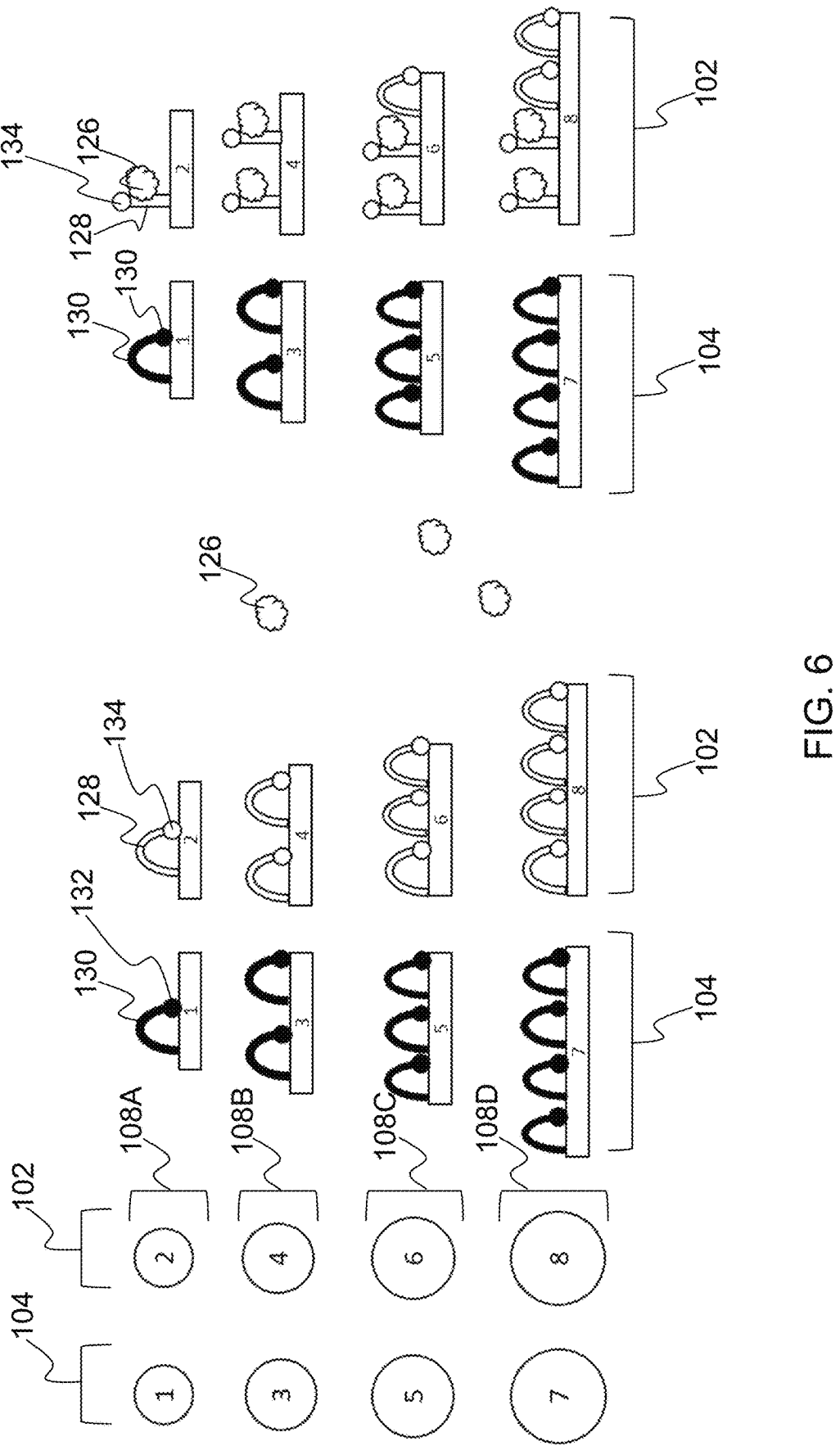
FIG. 6 schematically depicts analyte sensing using the sensing assembly shown in FIG. 4, when the analyte concentration in a sample matrix is relatively low.
Figure 7:
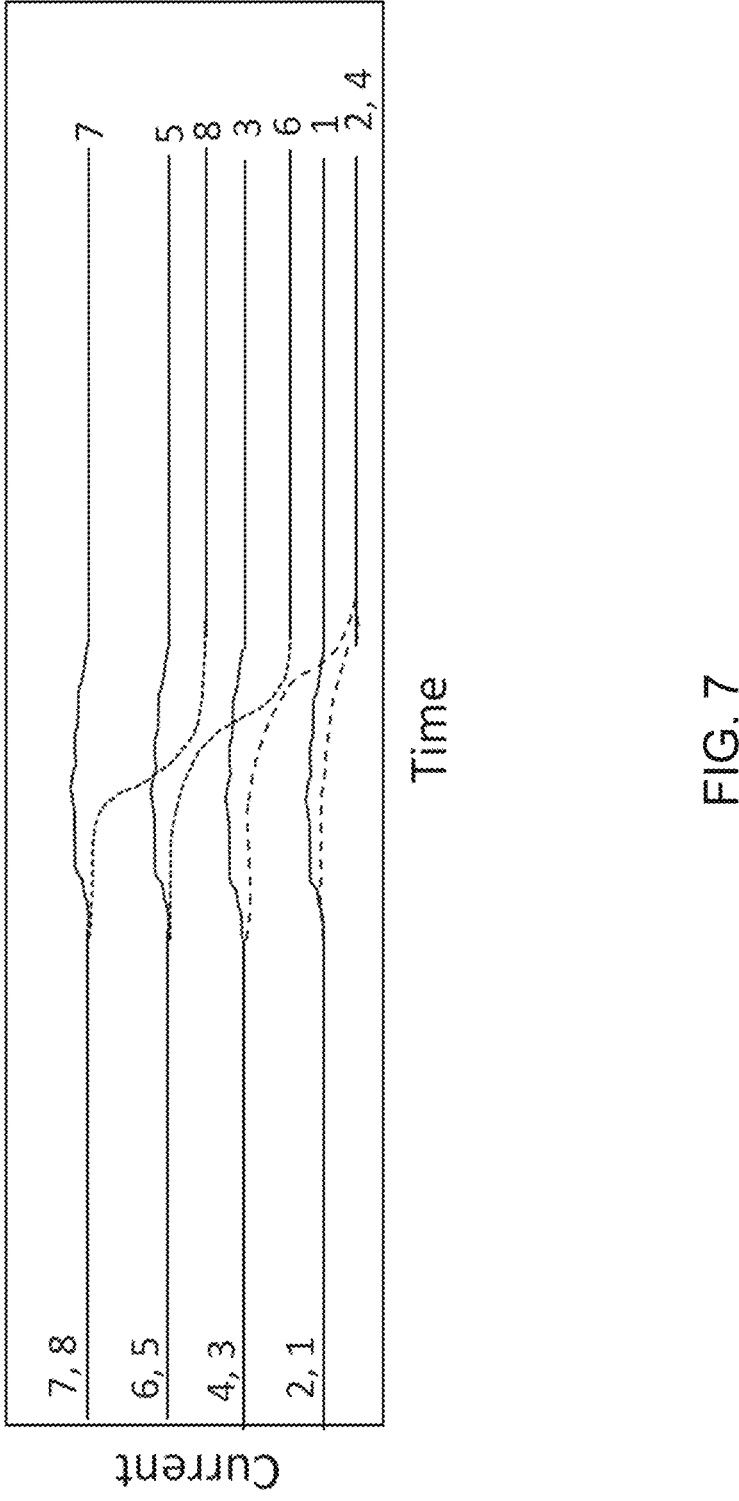
FIG. 7 provides graphs of sensor signal versus time for the sensing assembly and sample matrix shown in FIG. 6.

FIG. 6 schematically depicts analyte sensing using the sensing assembly 100 shown in FIG. 4 but when the analyte 126 concentration in the sample matrix is relatively low. FIG. 7 provides graphs of sensor signal versus time for the sensing assembly 100 and sample matrix shown in FIG. 6. In this case, the current approaches about zero current in fewer of the test electrodes 102 than in the relatively high concentration scenario of FIGS. 4 and 5. In particular, only the test electrodes numbered 2 and 4 in FIG. 6 become saturated such that the current falls to about zero. The test electrodes numbered 6 and 8 are not saturated with this lower analyte 126 concentration, and thus the current does not decrease to about zero current as it does for the test electrodes numbered 2 and 4.

Figure 8:
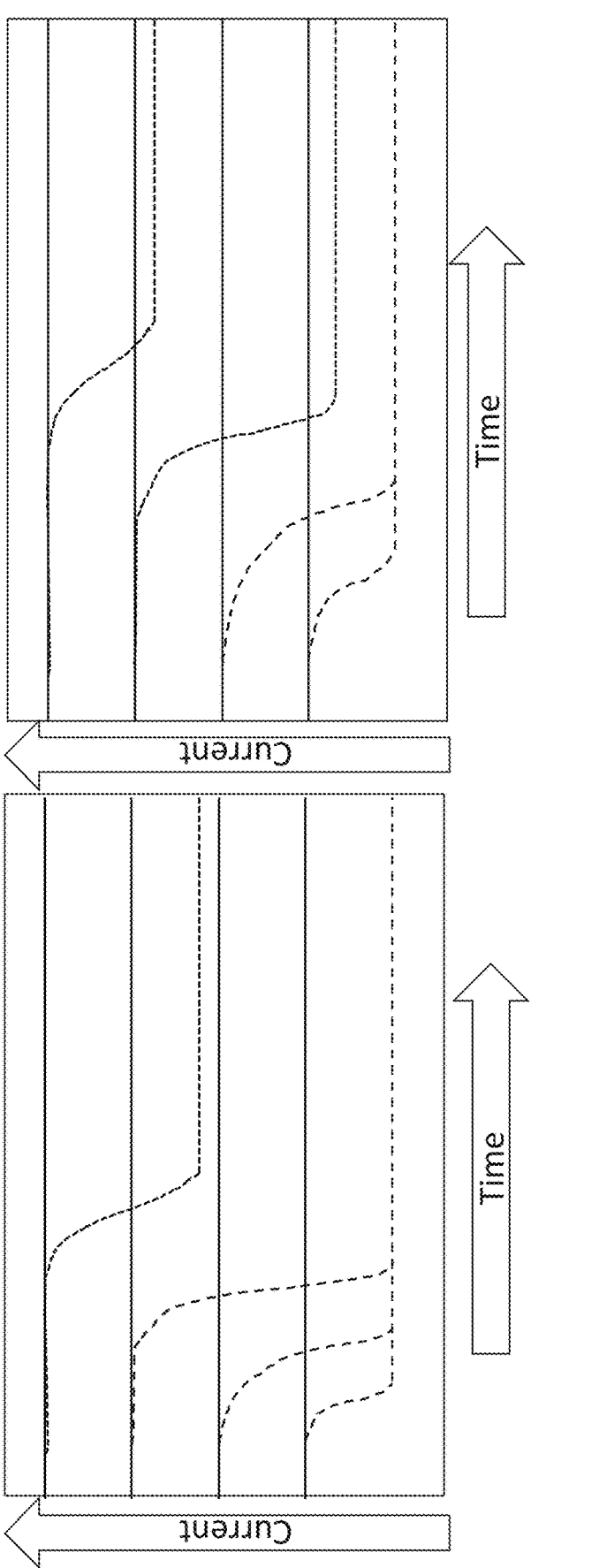
FIG. 8 provides simplified graphs of sensor signal versus time for a higher analyte concentration (left graph) and a lower analyte concentration (right graph)

FIG. 8 provides simplified graphs of sensor signal versus time for the higher analyte 126 concentration scenario of FIGS. 4 and 5 (left graph), and the lower analyte 126 concentration scenario of FIGS. 6 and 7 (right graph).

It is evident from FIG. 8 that higher analyte concentrations have the effect of increasing the rate of change of the signal, and increasing the number of test electrodes 102 in which the current decreases to about zero current. Conversely lower analyte concentrations lead to slower rates of signal changes, and fewer test electrodes 102 in which the current decreases to about zero current.

In other words, the absolute reduction in current may depend on the analyte concentration and the saturation limit of the test electrode 102, for example the functionalized area of the test electrode 102/the number of immobilized capture species. The rate of change of the current may also depend on the concentration.

Thus, these examples point to the absolute change in current from smaller to larger area test electrode-control electrode area pairs 108A, 108B, and different rates of change of the current permitting determination of the concentration of the analyte 126, for example by deconvolution of such multiple signal inputs, as previously described.

Whilst the set of control electrodes are depicted in FIGS. 1, 4 and 6 as an array, in particular a linear array, of control electrode areas 104, this is not intended to be limiting. FIG. 9 provides a schematic plan view of a set of control electrodes according to an alternative example. The set of control electrodes in this case comprises a plurality of portions, for example conductive portions, 138A, 138B, 138C which are each individually addressable. The set of control electrode areas 104 may each be defined by addressing one or more of the plurality of portions 138A, 138B, 138C.

Addressing/activating one, or certain combinations, of the portions, for example via a suitable switch arrangement (not visible in FIG. 9), may thus permit selection of each control electrode area. For example, the largest control electrode area may be provided by selecting all three portions 138A, 138B, 138C, and the smallest control electrode area may be selected by selecting only the smallest portion 138A. The control electrode area may, more generally, be selected according to the saturation limit of one of the test electrodes 102, as previously described.

As shown in FIG. 9, the portions 138A, 138B, 138C may be arranged in the form of concentric circular or elliptical portions 138A, 138B, 138C. In other non-limiting examples, the portions 138A, 138B, 138C may be arranged in other configurations, such as to form an interdigitated arrangement of portions 138A, 138B, 138C. Such arrangements may assist, for example, to save space on the substrate on which the set of control electrodes is arranged.

Whilst FIG. 9 shows three portions 138A, 138B, 138C, this is not intended to be limiting. Any number of portions 138A, 138B, 138C can be considered, such as two, four, five, six, seven, eight, or more. The number and size of the portions 138A, 138B, 138C may be selected according to the number and saturation limits, for example functionalized areas, of the test electrodes 102.

Figure 10:
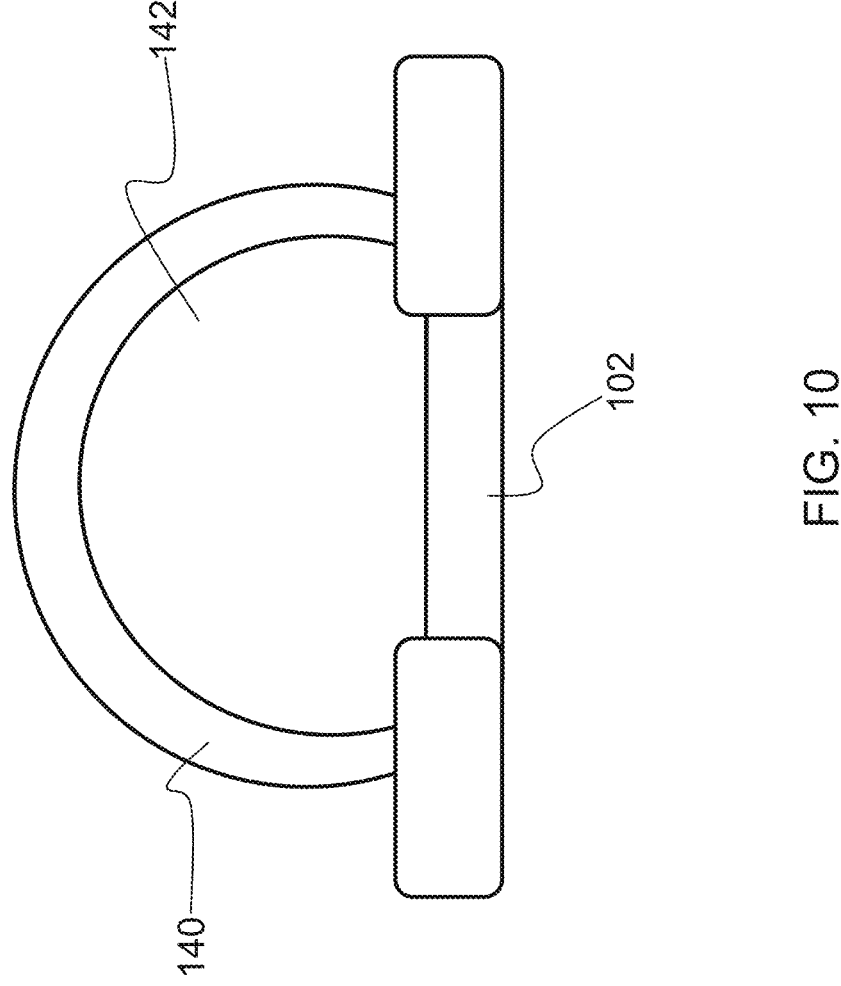
FIG. 10 schematically depicts a test electrode according to an example.

FIG. 10 schematically depicts a test electrode 102 according to an example in which the capture species are held adjacent the surface of the test electrode 102 by a membrane 140. The membrane 140 may permit the analyte to pass therethrough, and thereby be captured by the capture species disposed between the surface of the test electrode 102 and the membrane 140.

In such a non-limiting example, the parameter relating to an amount of the capture species for the respective test electrode 102 may comprise a concentration of the capture species in a solution 142 provided between the membrane 140 and the surface of the test electrode 102. By varying the concentration of the capture species in the solution 142 for each of the test electrodes 102, the saturation limits of the test electrodes can be varied.

In a specific non-limiting example, the capture species comprises, or is defined by, glucose oxidase, and the analyte is glucose. The glucose, and in this case oxygen, may pass, for example diffuse, through the membrane 140, and upon reaching the solution trapped between the membrane 140 and the test electrode 102, the glucose may be oxidized by the glucose oxidase, with concomitant reduction of the oxygen to hydrogen peroxide. The hydrogen peroxide can be quantified electrochemically via reduction to oxygen and hydrogen cations at the surface of the test electrode 102, such that the glucose concentration can be correspondingly determined.

Figure 11:
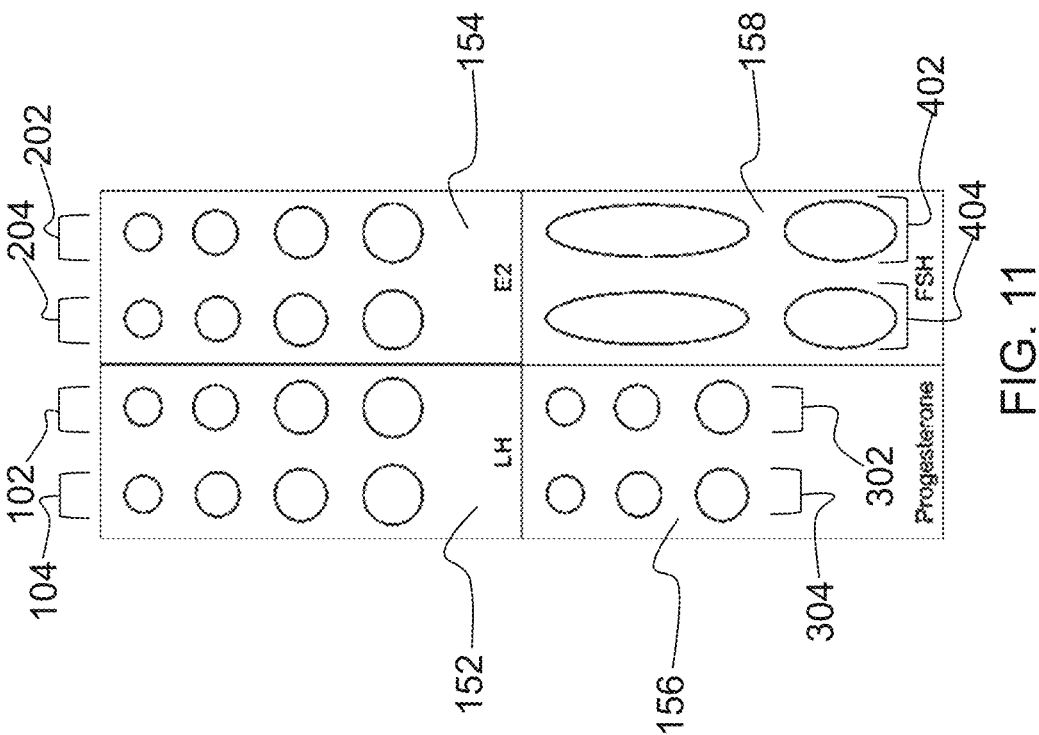
FIG. 11 schematically depicts an exemplary sensing assembly for sensing a plurality of analytes which are different from each other.

FIG. 11 schematically depicts an exemplary sensing assembly 100 for sensing a plurality of analytes which are different from each other. As shown in FIG. 11, the sensing assembly 100 comprises a first analyte testing portion 152, a second analyte testing portion 154, a third analyte testing portion 156, and a fourth analyte testing portion 158.

In the non-limiting example shown in FIG. 11, the first to fourth analyte testing portions 152 to 158 are conveniently provided on a common substrate, for example a common slide/chip/strip. In other examples, the analyte testing portions 152 to 158 can be provided on separate substrates.

The first analyte testing portion 152 comprises a first test electrode arrangement comprising a plurality of first test electrodes 102. Each of the first test electrodes 102 comprises a first analyte interaction portion configured to selectively interact with a first analyte, in this particular case luteinising hormone (LH). A first saturation limit at which the first analyte interaction portion is saturated with the first analyte is defined for each of the first test electrodes 102. The respective first saturation limits vary between the first test electrodes 102.

The first analyte testing portion 152 further comprises a first set of control electrodes providing a set of first control electrode areas 104, with each first control electrode area 104 being configured for providing a control measurement which is independent of each of the analytes. Each control electrode area 104 is provided for one of the first test electrodes 102.

The second analyte testing portion 154 comprises a second test electrode arrangement comprising a plurality of second test electrodes 202 having varying saturation limits and configured to selectively interact with a second analyte, in this particular case estradiol (E-2). The second analyte testing portion 154 also comprises a second set of control electrodes providing a set of second control electrode areas 204, with each second control electrode area 204 being provided for one of the second test electrodes 202.

The third analyte testing portion 156 comprises a third test electrode arrangement comprising a plurality of third test electrodes 302 having varying saturation limits and configured to selectively interact with a third analyte, in this particular case progesterone. The third analyte testing portion 156 also comprises a third set of control electrodes providing a set of third control electrode areas 304, with each third control electrode area 304 being provided for one of the third test electrodes 302.

The fourth analyte testing portion 158 comprises a fourth test electrode arrangement comprising a plurality of fourth test electrodes 402 having varying saturation limits and configured to selectively interact with a fourth analyte, in this particular case follicle-stimulating hormone (FSH). The fourth analyte testing portion also comprises a fourth set of control electrodes providing a set of fourth control electrode areas 404, with each fourth control electrode area 404 being provided for one of the fourth test electrodes 402.

Table 1 provides the concentration range of the first to fourth analytes which can be sensed by the sensing assembly 100 according to the non-limiting example depicted in FIG. 11.

TABLE 1

| ANALYTE | RANGE (g/L) | |
| --- | --- | --- |
| Estradiol (E-2) | 1.00E−09 | 1.00E−06 |
| Luteinising hormone (LH) | 4.65E−08 | 4.65E−06 |
| Progesterone | 1.00E−09 | 1.00E−07 |
| Follicle-stimulating hormone (FSH) | 1.14E−04 | 1.14E−02 |

Multiple signals generated for each of the first to fourth analytes can be used to determine their concentration, for example using a suitable algorithm that accounts for the absolute change in signals in the test electrode-control electrode pairs, and the rate of change of the signals, as previously described.

Such a sensing assembly 100 may, for example, enable concentrations of the plurality of analytes to be measured regularly, for example daily. Such concentrations could then tracked, and in some examples uploaded and an individual user profile generated based on the uploaded concentrations. In this manner, the concentrations obtained via the sensing assembly 100 can be used for, for instance, clinical decisions regarding dose and/or timing of administration of the dose.

Figure 12:
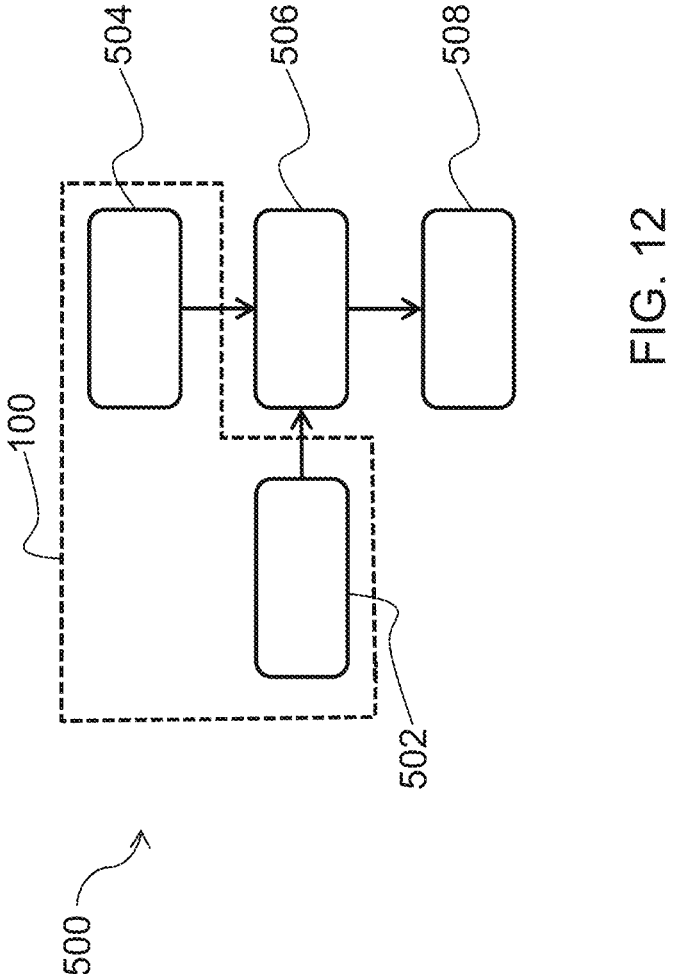
FIG. 12 provides a block diagram of a system according to an example.

FIG. 12 provides a block diagram of a system 500 according to an example. The system 500 is for determining a concentration of an analyte in a sample matrix. The system 500 comprises a sensing assembly 100 for sensing the analyte. The sensing assembly 100 comprises a test electrode arrangement 502. The test electrode arrangement 502 comprises a plurality of test electrodes 102. Each of the test electrodes 102 has an analyte interaction portion configured to selectively interact with the analyte. A saturation limit at which the analyte interaction portion is saturated with the analyte is defined for each of the test electrodes 102. The respective saturation limits vary between the test electrodes 102. The sensing assembly 100 further comprises a set of control electrodes 504 providing a set of control electrode areas 104, with each control electrode area 104 being provided for one of the test electrodes 102.

The sensing assembly 100 included in the system 500 may thus be according to any of the examples and embodiments described herein.

The system 500 also comprises a signal processing unit 506 and a concentration determination unit 508. The signal processing unit 506 is configured to process signals received from the plurality of test electrodes 102, and process signals received from the set of control electrode areas 104. The concentration determination unit 508 is configured to, based on the signals processed from the plurality of test electrodes and on the signals processed from the set of control electrode areas 104, determine the concentration of the analyte in the sample matrix.

In at least some embodiments, the concentration determination unit 508 is configured to determine the concentration based on one or more differential signals from the signals processed from the plurality of test electrodes 102 and the signals processed from the set of control electrode areas 104.

In a non-limiting example, the concentration determination unit 508 is configured to determine the concentration based on the absolute change in signals in the test electrode-control electrode pairs 108A, 108B, 108C, 108D, and the rate of change of the signals.

Whilst not visible in FIG. 12, a user interface, such as a display, for communicating the analyte concentration determined by the concentration determination unit 508 may be included in the system 500. Alternatively or additionally, the system 500 may include a transmitter (also not visible in FIG. 12), such as a wireless transmitter, configured to transmit the analyte concentration determined by the concentration determination unit 508 to an external device, such as a personal computer, tablet, smartphone, remote server, etc.

Figure 13:
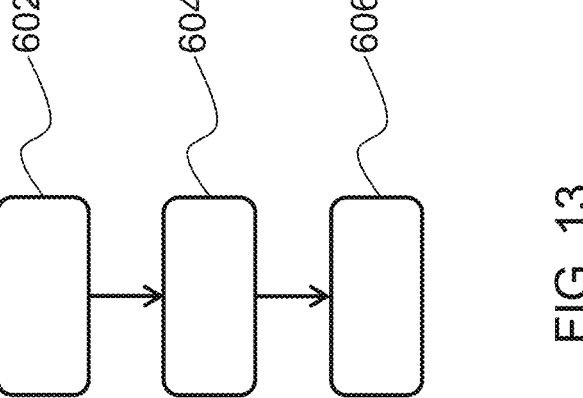
FIG. 13 shows a flowchart of a method according to an example.

FIG. 13 shows a flowchart of a method 600 according to an example. The method 600 is for determining a concentration of an analyte in a sample matrix. The method comprises, in block 602, processing signals received from a plurality of test electrodes. Each of the test electrodes comprises an analyte interaction portion configured to selectively interact with the analyte. A saturation limit at which the analyte interaction portion is saturated with the analyte is defined for each of the test electrodes, and the respective saturation limits vary between the test electrodes.

The method 600 also comprises, in block 604, processing signals received from a set of control electrodes. The set of control electrodes provides a set of control electrode areas, with each control electrode area being configured for providing a control measurement which is independent of the analyte; each control electrode area being provided for one of the test electrodes.

In block 606, the concentration of the analyte in the sample matrix is determined based on the signals processed from the plurality of test electrodes and on the signals processed from the set of control electrodes.

In some embodiments, the determining 606 the concentration of the analyte comprises determining one or more differential signals from the signals processed from the plurality of test electrodes and the signals processed from the set of control electrodes.

In a non-limiting example, the determining 606 is based on the absolute change in signals in the test electrode-control electrode pairs, and the rate of change of the signals.

The method 600 may, for example, employ the sensing assembly 100 and/or the system 500 according to any of the embodiments and examples described herein.

In particular, the method 600 may be implemented using the signal processing unit 506 and the concentration determination unit 508 of the system 500 of the present disclosure.

In certain embodiments, a computer program comprising computer program code is adapted, when the program is run on a computer, to implement the method 600 according to any of the examples and embodiments described herein. Such a computer may, for example, be included in, or define, the signal processing unit 506 and the concentration determination unit 508 of the system 500 of the present disclosure. The computer program may be stored on one or more non-transitory computer readable media. The computer program may include instructions, when executed by one or more physical computing devices such as one or more processors, can cause the one or more processors to implement, execute and/or carry out one or more methods described herein.

More generally, examples and embodiments described herein in respect of the sensing assembly 100 may be applicable to the system 500, method 600 and/or computer program. Similarly, examples and embodiments described herein in respect of the system 500, method 600 and/or computer program may be applicable to the sensing assembly 100.

Figure 14:
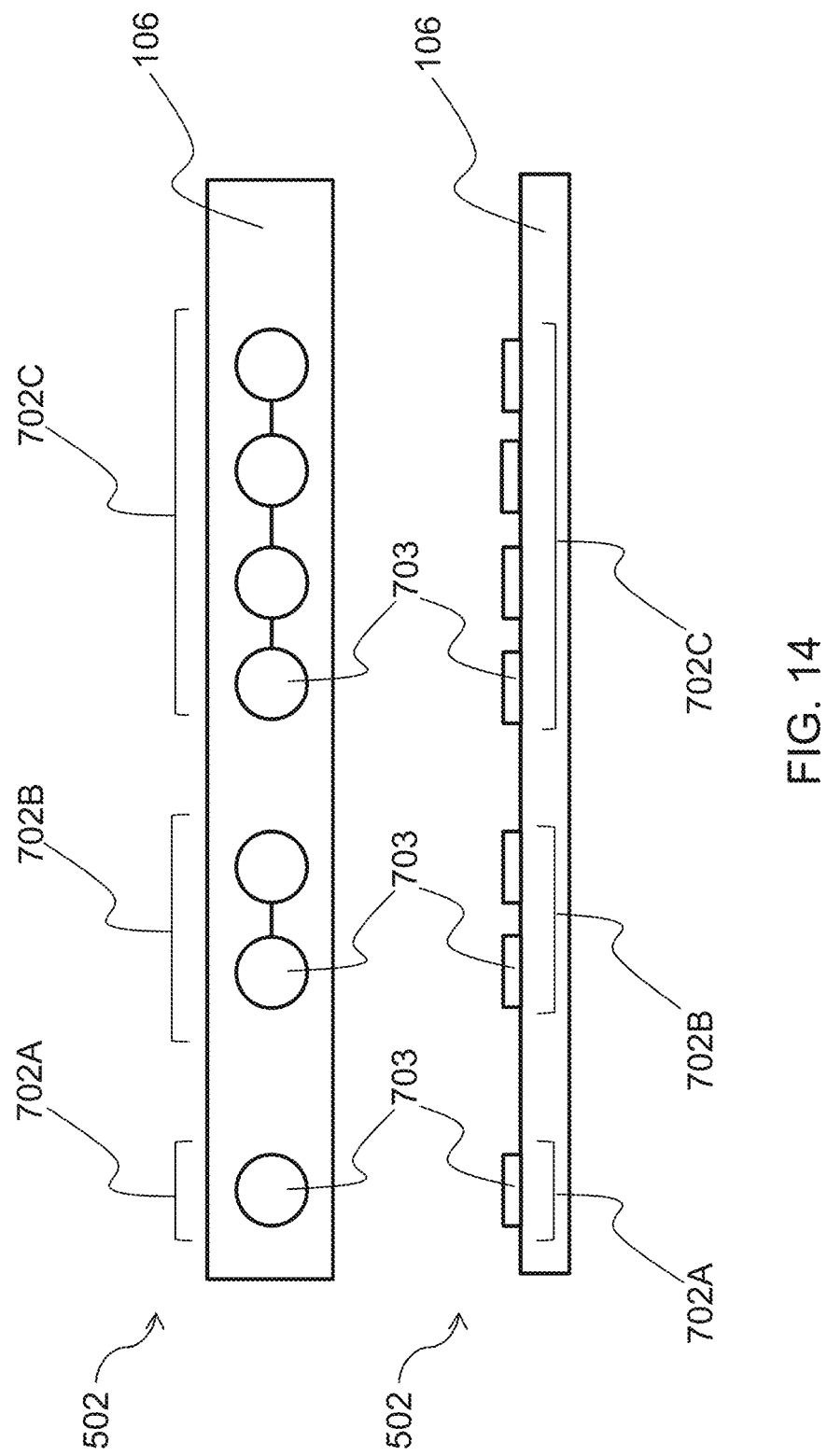
FIG. 14 provides views of an exemplary test electrode arrangement having test electrode units and sub-units.

FIG. 14 provides views of a test electrode arrangement 502 according to a non-limiting example. The depicted test electrode arrangement 502 comprises a plurality of units 702A, 702B, 702C, with each unit 702A, 702B, 702C defining one of the test electrodes and comprising a number of test electrode sub-units 703. The number of test electrode sub-units 703 in each unit 702A, 702B, 702C at least partly determines the saturation limit of the respective test electrode.

When the respective unit 702B, 702C comprises more than one test electrode sub-unit 703, the test electrode sub-units 703 of the respective unit 702B, 702C may be connected to each other, as shown in FIG. 14.

The units 702A, 702B, 702C in the example shown in FIG. 14 are provided on a common substrate 106. It is nonetheless noted that in other examples at least some of the units 702A, 702B, 702C can be provided on a different substrate from the other units 702A, 702B, 702C.

The test electrode sub-units 703 are arranged in a linear fashion for each unit 702A, 702B, 702C in the example shown in FIG. 14. This spatial arrangement may facilitate functionalization of the test electrode sub-units 703, for example when reagent is to be dropped onto more than one of the test electrode sub-units 703 at the same time. Alternative spatial arrangements of the test electrode sub-units 703 are nonetheless conceivable, for example in order to save space on the substrate 106.

As shown in FIG. 14, unit 702A has a single test electrode sub-unit 703, unit 702B has two test electrode sub-units 703, and unit 702C has four test electrode sub-units 703. More generally, any number of test electrode sub-units 703 per unit 702A, 702B, 702C can be contemplated in order to enable varying of the saturation limit of the units 702A, 702B, 702C without necessarily requiring different functionalization protocols/reagents to be used to fabricate each unit 702A, 702B, 702C.

In the non-limiting example shown in FIG. 14, each of the test electrode sub-units 703 have the same area as each other. This may, for instance, enable the same reagent drop size, reagents, washes, etc., to be used for each of these test electrode sub-units 703.

Figure 15:
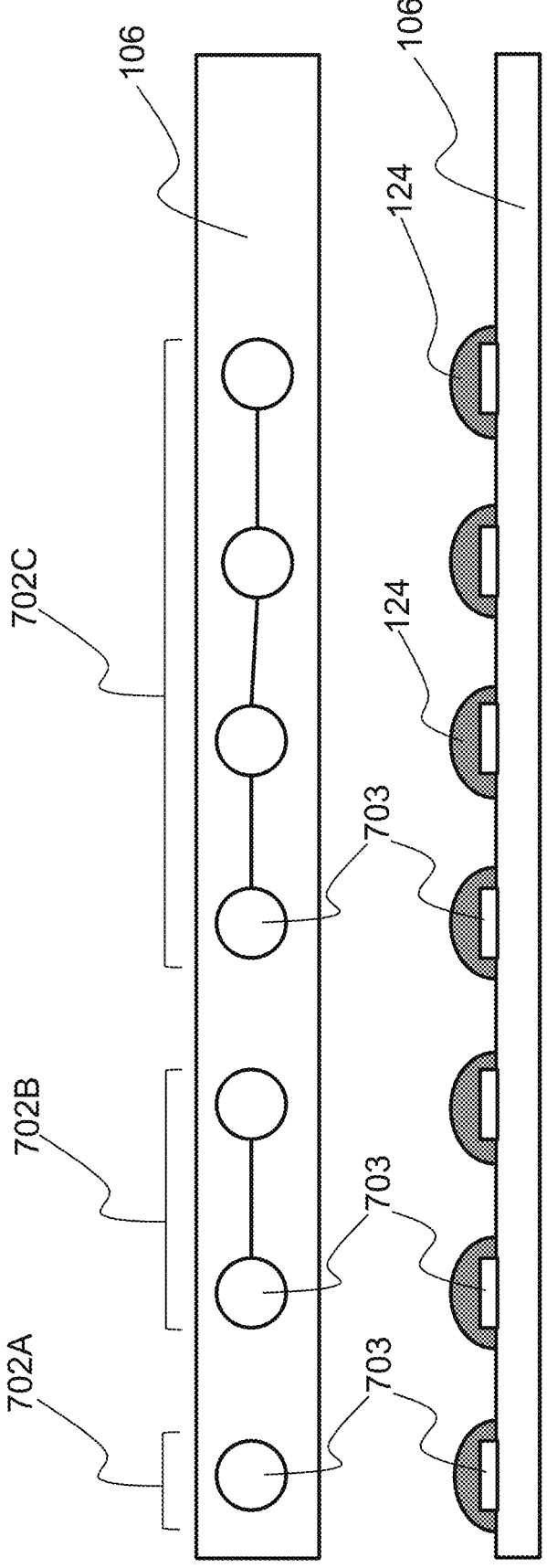
FIG. 15 provides a schematic plan view of test electrode units and sub-units according to another example, and a schematic depiction of immobilization of a capture species on the test electrode sub-units.

In this respect, FIG. 15 schematically depicts an exemplary functionalization process in which the same reagent drop size 124 is used for each of the test electrodes sub-units 703. This may provide a convenient way of realizing units 702A, 702B, 702C with varying saturation limits.

The drop size 124, for example the largest diameter of each drop in a plane parallel with the surface of the substrate 106, may be, for example, 10 μm to 150 μm, such as 50 μm to 150 μm, such as 100 μm. The area of each of the test electrode sub-units 703 may, for instance, range from 1 μm to 100 μm, such as 10 μm to 100 μm.

More generally, at least some of the units 702A, 702B, 702C may have sub-units 703 designed to have overlapping analyte depletion diffusion/mass transport areas so that the respective unit 702A, 702B, 702C may act as a single larger test electrode with varying transient response.

Alternatively or additionally, at least some of the units 702A, 702B, 702C may have sub-units 703 which are physically spaced from each other in the respective unit 702A, 702B, 702C, so as not to have overlapping analyte depletion diffusion/mass transport areas. Such units 702A, 702B, 702C may each act as a larger area electrode with relatively constant transient responses.

Figures 16, 17, 18:
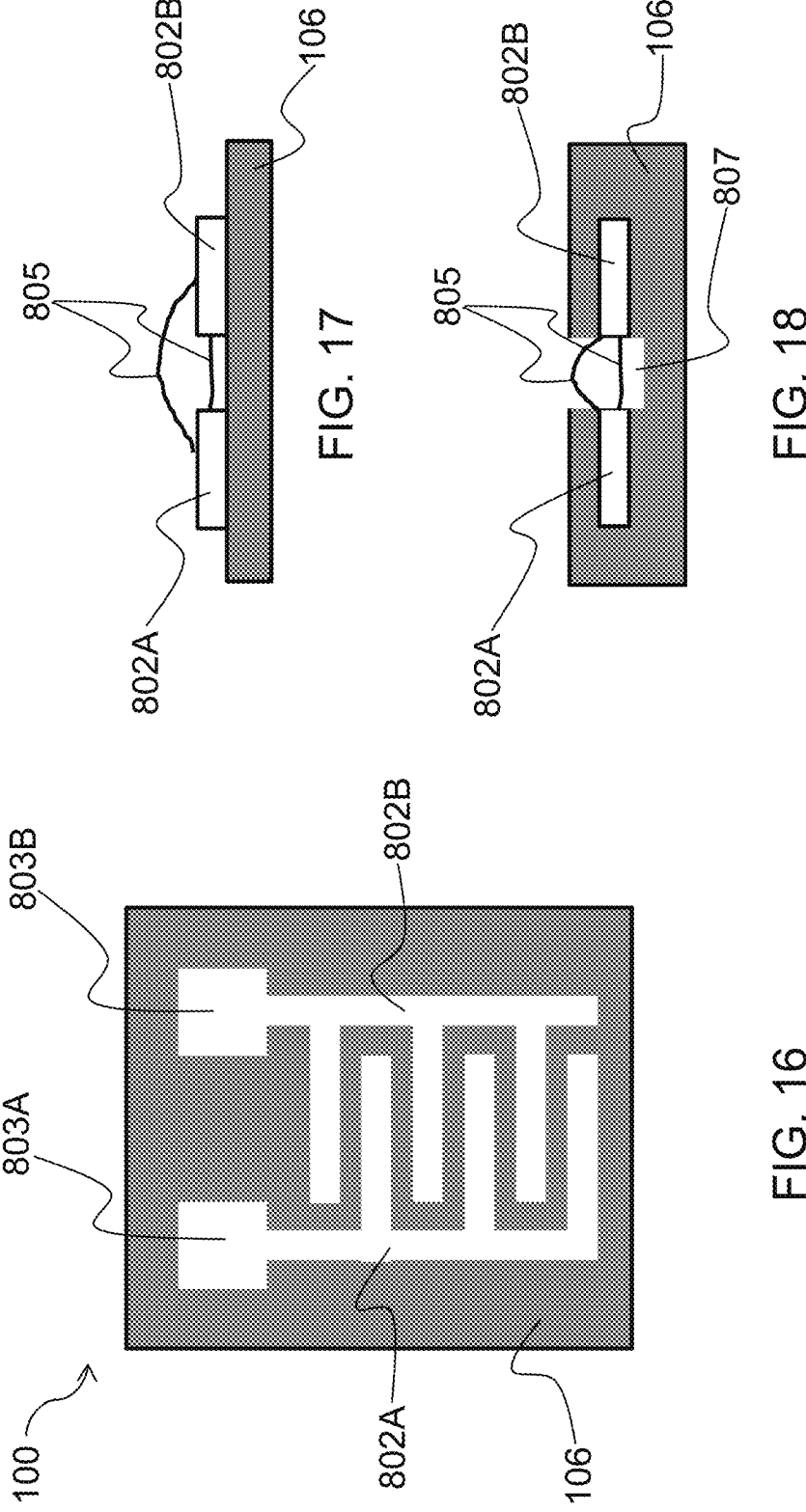
FIGS. 16 to 18 provide views of a sensing assembly according to further examples.

FIGS. 16 to 18 schematically depict views of exemplary sensing assemblies 100 which each comprise a capacitance and/or impedance determination assembly.

Such a capacitance and/or impedance determination assembly may comprise a further electrode arrangement 802A, with at least some of the test electrodes 802B of the test electrode arrangement being spaced apart from the further electrode arrangement such as to enable determination of capacitance and/or impedance between said at least some of the test electrodes 802B and the further electrode arrangement 802A. The test electrodes have varying saturation limits, as previously described.

The further electrode arrangement 802A and said at least some of the test electrodes 802B may be arranged relative to each other in any suitable manner, such as using the interdigitated arrangement schematically depicted in FIG. 16.

As shown in FIG. 16, the further electrode arrangement 802A may extend from a first contact 803A, and said at least some of the test electrodes 802B may extend from a second contact 803B. In this non-limiting example, the first and second contacts 803A, 803B, and the electrode arrangements 802A, 802B are arranged on a common substrate 106, such as a common semiconductor substrate.

In the non-limiting example shown in FIG. 16, the further electrode arrangement 802A itself comprises one or more of the test electrodes, such that each of the spatially separated interdigitated "plates" of the capacitance and/or impedance determination assembly comprises the analyte interaction portion, for example in the form of a surface functionalized with the above-described capture species.

In the example shown in FIG. 17, which shows a cross-section of part of the capacitance and/or impedance determination assembly, the electrode arrangements 802A, 802B are both proud of the surface of the substrate 106. The electric field is thus provided above the surface of the substrate 106, with the electric field lines 805 extending over the gap provided between the electrode arrangements 802A, 802B.

In the alternative non-limiting example shown in FIG. 18, a trench 807 is provided between the electrode arrangements 802A, 802B. In this example, the electrode arrangements 802A, 802B, for example interdigitated electrode arrangements 802A, 802B, may be set into the substrate 106, as shown.

It should be understood that the detailed description and specific examples, while indicating exemplary embodiments of the apparatus, systems and methods, are intended for purposes of illustration only and are not intended to limit the scope. These and other features, aspects, and advantages of the apparatus, systems and methods of the present invention can be better understood from the description, appended claims, and accompanying drawings. It should be understood that the Figures are merely schematic and are not drawn to scale. It should also be understood that the same reference numerals are used throughout the figures to indicate the same or similar parts.

Other variations to the disclosed embodiments can be understood and effected by those skilled in the art in practicing the disclosure, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensing assembly to sense an analyte, the sensing assembly comprising:

a test electrode arrangement comprising a plurality of test electrodes, each electrode of the plurality of test electrodes comprising an analyte interaction portion configured to selectively interact with the analyte, a saturation limit at which the analyte interaction portion is saturated with the analyte being defined for each electrode of the plurality of test electrodes, wherein the respective saturation limits for the same analyte vary between electrodes of the plurality of test electrodes; and a set of control electrodes providing a set of control electrode areas, each control electrode area in the set of control electrode areas being configured to provide a control measurement which is independent of the analyte, wherein each control electrode area in the set of control electrode areas is provided for one of the plurality of test electrodes.

2. The sensing assembly according to claim 1, wherein the set of control electrode areas vary relative to each other.

3. The sensing assembly according to claim 2, wherein the varying of the set of control electrode areas permits an ordering of the set of control electrode areas by increasing size, and the varying of the saturation limits permits a second ordering of the plurality of test electrodes by increasing saturation limit, a series of test electrode-control electrode area pairs being defined according to the ordering and the second ordering such that the smallest control electrode area is paired with the test electrode having the smallest saturation limit to the largest control electrode area being paired with the test electrode having the largest saturation limit.

4. The sensing assembly according to claim 3, wherein, for consecutive test electrode-control electrode area pairs of the series, an incremental change in the set of control electrode areas corresponds to a further incremental change in the saturation limits of the plurality of test electrodes.

5. The sensing assembly according to claim 1, wherein each analyte interaction portion is defined by capture species provided adjacent a surface of a respective test electrode, said capture species being configured to selectively interact with the analyte.

6. The sensing assembly according to claim 5, wherein the capture species comprises at least one capture species selected from a protein, a peptide, a carbohydrate, and a nucleic acid.

7. The sensing assembly according to claim 5, wherein the capture species comprises an aptamer.

8. The sensing assembly according to claim 5, wherein said surface is functionalized with the capture species, wherein a parameter relating to an amount of the capture species for each electrode of the plurality of test electrodes at least partly determines the saturation limit of the respective test electrode, and wherein the parameter comprises at least one of an area of the surface functionalized with the capture species and a density of the capture species on said surface.

9. The sensing assembly according to claim 8, wherein each control electrode area corresponds to the area of the surface of one of the plurality of test electrodes functionalized with the capture species.

10. The sensing assembly according to claim 5, wherein the capture species are held adjacent the surface by a membrane, wherein a parameter relating to an amount of the capture species for each electrode of the plurality of test electrodes at least partly determines the saturation limit of the respective test electrode, and wherein the parameter comprises a concentration of the capture species in a solution provided between the membrane and the surface.

11. The sensing assembly according to claim 1, wherein the set of control electrodes comprises a plurality of portions which are each individually addressable, and wherein the set of control electrode areas are each defined by addressing one or more of the plurality of portions.

12. The sensing assembly according to claim 1, wherein the test electrode arrangement comprises a plurality of units, each unit of the plurality of units defining one of the test electrodes and comprising a number of test electrode sub-units, and wherein the number of test electrode sub-units in each unit of the plurality of units at least partly determines the saturation limit of the respective test electrode.

13. The sensing assembly according to claim 1, wherein the test electrode arrangement and the set of control electrodes are arranged to receive a sample matrix suitable for containing the analyte, and wherein the control electrode areas in the set of control electrode areas are configured for non-selective interaction with the sample matrix.

14. The sensing assembly according to claim 1, wherein the test electrode arrangement and the set of control electrodes are arranged to receive a sample matrix suitable for containing the analyte, and wherein the control electrode areas in the set of control electrode areas are configured to selectively interact with a non-analyte species included in the sample matrix.

15. The sensing assembly according to claim 1, comprising an electrochemical cell including a working electrode assembly and a counterelectrode, wherein the working electrode assembly comprises the test electrode arrangement, the test electrode arrangement being configured to determine a change in current associated with said selective interaction with the analyte.

16. The sensing assembly according to claim 15, wherein the test electrode arrangement and the set of control electrodes are arranged to receive a sample matrix suitable for containing the analyte, and wherein the working electrode assembly comprises the set of control electrodes, the set of control electrodes being configured to determine a change in current associated with the sample matrix contacting said set of control electrode areas.

17. The sensing assembly according to claim 1, comprising a capacitance and/or impedance determination assembly comprising the test electrode arrangement, and wherein the capacitance and/or impedance determination assembly comprises a second electrode arrangement, at least some of the plurality of test electrodes of the test electrode arrangement being spaced apart from the second electrode arrangement such as to enable determination of capacitance and/or impedance between said at least some of the plurality of test electrodes of the test electrode arrangement and the second electrode arrangement.

18. A system to determine a concentration of an analyte in a sample matrix, the system comprising:

the sensing assembly of claim 1; and a signal processing unit configured to:

process signals received from the plurality of test electrodes, resulting in first processed signals; and process signals received from the set of control electrode areas, resulting in second processed signals; and a concentration determination unit configured to, based on the first processed signals and on the second processed signals, determine said concentration of the analyte in the sample matrix.

19. A method for determining a concentration of an analyte in a sample matrix using the sensing assembly of claim 1, the method comprising:

processing signals received from the plurality of test electrodes, resulting in first processed signals;

processing signals received from the set of control electrodes, resulting in second processed signals; and determining said concentration of the analyte in the sample matrix based on the first processed signals and on the second processed signals.

\* \* \* \* \*